(12) United States Patent
Ryaboy et al.

(10) Patent No.: US 8,231,098 B2
(45) Date of Patent: *Jul. 31, 2012

(54) METHODS AND DEVICES FOR ACTIVE VIBRATION DAMPING OF AN OPTICAL STRUCTURE

(75) Inventors: Vyacheslav M. Ryaboy, Irvine, CA (US); Prakash S. Kasturi, Rancho Santa Margarita, CA (US); Adrian S. Nastase, Huntington Beach, CA (US)

(73) Assignee: Newport Corporation, Irvine, CA (US)

( * ) Notice: Subject to any disclaimer, the term of this patent is extended or adjusted under 35 U.S.C. 154(b) by 820 days.

This patent is subject to a terminal disclaimer.

(21) Appl. No.: 11/293,439

(22) Filed: Dec. 2, 2005

(65) Prior Publication Data
US 2006/0119026 A1 Jun. 8, 2006

Related U.S. Application Data

(60) Provisional application No. 60/634,227, filed on Dec. 7, 2004.

(51) Int. Cl.
*F16M 13/00* (2006.01)
(52) U.S. Cl. .................. 248/550; 248/638; 188/378
(58) Field of Classification Search .............. 248/550, 248/636–638, 639, 559, 645, 646; 267/140.14, 267/136, 140.11, 140.15, 140.3, 140.2; 188/378, 188/379, 380
See application file for complete search history.

(56) References Cited

U.S. PATENT DOCUMENTS

| | | | |
|---|---|---|---|
| 1,143,165 A | 6/1915 | Begusch | |
| 1,306,906 A | 6/1919 | Jaques, Sr. | |
| 2,351,386 A | 6/1944 | Zucker | |
| 2,367,139 A | 1/1945 | Ress | |
| 3,357,268 A | 12/1967 | Richter | |
| 3,442,475 A | 5/1969 | Rivin | |
| 3,460,786 A | 8/1969 | Rivin | |
| 3,478,608 A | 11/1969 | Met | |
| 3,533,012 A | 10/1970 | Johnson et al. | |

(Continued)

FOREIGN PATENT DOCUMENTS

CA 2199423 3/1996

(Continued)

OTHER PUBLICATIONS

J. M. Kahn, C. A. Burrus, and G. Raybon, High-Stability 1.5 um External-Cavity Semiconductor Lasers for Phase-Lock Applications, Photonics Technology Letters, vol. 1. No. 7, Jul. 1989.

(Continued)

*Primary Examiner* — Tan Le
(74) *Attorney, Agent, or Firm* — Grant Anderson LLP

(57) ABSTRACT

A vibration damper assembly that may be attached and moved about a payload or optical mount surface of an optical structure such as an optical table. The vibration damper assembly may include a sensor and an actuator that may be disposed within a housing. In some embodiments, the vibration damper assembly or components thereof may be incorporated into an optical structure in the form of an optical component to be disposed or mounted on an optical mount surface of an optical structure such as an optical table. Embodiments of the vibration damper system may include a controller in communication with the damper assembly Embodiments of the controller may use adaptive tuning, autoranging selection of gain factors and other features in order to optimize damping performance.

10 Claims, 17 Drawing Sheets

U.S. PATENT DOCUMENTS

| | | |
|---|---|---|
| 3,565,515 A | 2/1971 | De Mey, II |
| 3,577,791 A | 5/1971 | Vanden Broek |
| 3,578,278 A | 5/1971 | Pickering |
| 3,601,476 A | 8/1971 | MacKenzie |
| 3,620,558 A | 11/1971 | MacMillan |
| 3,667,525 A | 6/1972 | Spieth |
| 3,751,025 A | 8/1973 | Beery et al. |
| 3,784,146 A | 1/1974 | Mathews |
| 3,917,201 A | 11/1975 | Roll |
| 3,945,246 A | 3/1976 | Wadensten |
| 3,989,358 A | 11/1976 | Melmoth |
| 4,030,811 A | 6/1977 | Khoe et al. |
| 4,065,203 A | 12/1977 | Goell et al. |
| 4,079,404 A | 3/1978 | Comerford et al. |
| 4,083,433 A | 4/1978 | Geohegan, Jr. et al. |
| 4,088,396 A | 5/1978 | Edelstein |
| 4,119,363 A | 10/1978 | Camlibel et al. |
| 4,144,504 A | 3/1979 | Leggett et al. |
| 4,146,329 A | 3/1979 | King et al. |
| 4,164,151 A | 8/1979 | Nolan et al. |
| 4,164,363 A | 8/1979 | Hsu |
| 4,167,744 A | 9/1979 | Nyul |
| 4,199,222 A | 4/1980 | Ikushima et al. |
| 4,237,474 A | 12/1980 | Ladany |
| 4,268,113 A | 5/1981 | Noel, Jr. |
| 4,295,152 A | 10/1981 | Khoe et al. |
| 4,296,998 A | 10/1981 | Dufft |
| 4,316,678 A | 2/1982 | F'Geppert |
| 4,332,469 A | 6/1982 | Wendland |
| 4,350,867 A | 9/1982 | Kinoshita et al. |
| 4,355,323 A | 10/1982 | Kock |
| 4,357,072 A | 11/1982 | Goodfellow et al. |
| 4,387,956 A | 6/1983 | Cline |
| 4,403,243 A | 9/1983 | Hakamada |
| 4,435,037 A | 3/1984 | Abramson et al. |
| 4,469,399 A | 9/1984 | Cowen et al. |
| 4,469,929 A | 9/1984 | Rosen et al. |
| 4,479,698 A | 10/1984 | Landis et al. |
| 4,494,720 A | 1/1985 | Gregory et al. |
| 4,500,032 A | 2/1985 | Ackerman |
| 4,500,165 A | 2/1985 | Scholl et al. |
| 4,506,108 A | 3/1985 | Kersch et al. |
| 4,514,849 A | 4/1985 | Witte et al. |
| 4,515,337 A | 5/1985 | Torras |
| 4,523,802 A | 6/1985 | Sakaguchi et al. |
| 4,523,810 A | 6/1985 | Goss et al. |
| 4,525,659 A | 6/1985 | Imahashi et al. |
| 4,550,410 A | 10/1985 | Chenausky et al. |
| 4,576,480 A | 3/1986 | Travis |
| 4,586,743 A | 5/1986 | Edwards et al. |
| 4,615,031 A | 9/1986 | Eales et al. |
| 4,618,759 A | 10/1986 | Muller et al. |
| 4,621,006 A | 11/1986 | Terry et al. |
| 4,623,220 A | 11/1986 | Grabbe et al. |
| 4,645,171 A | 2/1987 | Heide |
| 4,647,147 A | 3/1987 | Pikulski et al. |
| 4,647,331 A | 3/1987 | Koury, Jr. et al. |
| 4,656,641 A | 4/1987 | Scifres et al. |
| 4,657,429 A | 4/1987 | Morris |
| 4,664,732 A | 5/1987 | Campbell et al. |
| 4,673,244 A | 6/1987 | Miles |
| 4,673,245 A | 6/1987 | Kling et al. |
| 4,677,290 A | 6/1987 | Mitch |
| 4,678,271 A | 7/1987 | Beaulieu |
| 4,679,908 A | 7/1987 | Goodwin |
| 4,687,287 A | 8/1987 | Lukas et al. |
| 4,701,013 A | 10/1987 | Jurczyszyn et al. |
| 4,702,556 A | 10/1987 | Ishii et al. |
| 4,706,920 A | 11/1987 | Ojima et al. |
| 4,708,429 A | 11/1987 | Clark et al. |
| 4,714,315 A | 12/1987 | Krause |
| 4,720,163 A | 1/1988 | Goodwin et al. |
| 4,729,239 A | 3/1988 | Gordon |
| 4,746,195 A | 5/1988 | Auracher et al. |
| 4,747,657 A | 5/1988 | Chaoui et al. |
| 4,748,632 A | 5/1988 | Preston |
| 4,759,600 A | 7/1988 | Caron et al. |
| 4,763,979 A | 8/1988 | Heywang |
| 4,767,174 A | 8/1988 | Carenco et al. |
| 4,773,730 A | 9/1988 | Sedlmayr |
| 4,779,946 A | 10/1988 | Pimpinella et al. |
| 4,779,959 A | 10/1988 | Saunders |
| 4,782,223 A | 11/1988 | Suzuki |
| 4,787,691 A | 11/1988 | Lorenzo et al. |
| 4,800,262 A | 1/1989 | Lentine |
| 4,807,750 A | 2/1989 | Ryder et al. |
| 4,818,173 A | 4/1989 | Khusro |
| 4,823,220 A | 4/1989 | Milster et al. |
| 4,837,768 A | 6/1989 | Schmid |
| 4,839,961 A | 6/1989 | Vermeer |
| 4,842,397 A | 6/1989 | Eisler |
| 4,850,261 A | 7/1989 | Greene |
| 4,850,671 A | 7/1989 | Finzel |
| 4,854,667 A | 8/1989 | Ebata et al. |
| 4,870,631 A | 9/1989 | Stoddard |
| 4,881,863 A | 11/1989 | Braginsky |
| 4,890,715 A | 1/1990 | Sticht |
| 4,913,527 A | 4/1990 | Jessop |
| 4,914,797 A | 4/1990 | Tsuchida et al. |
| 4,914,867 A | 4/1990 | Saito et al. |
| 4,915,482 A | 4/1990 | Collins et al. |
| 4,916,635 A | 4/1990 | Singer et al. |
| 4,938,564 A | 7/1990 | Romero |
| 4,947,335 A | 8/1990 | Blitchington |
| 4,966,474 A | 10/1990 | Geiger |
| 4,978,910 A | 12/1990 | Knox et al. |
| 4,987,293 A | 1/1991 | Baciak |
| 4,988,159 A | 1/1991 | Turner et al. |
| 4,988,165 A | 1/1991 | Ishii et al. |
| 5,000,415 A | 3/1991 | Sandercock |
| 5,033,061 A | 7/1991 | Hobart et al. |
| 5,044,719 A | 9/1991 | Nakamura |
| 5,058,124 A | 10/1991 | Cameron et al. |
| 5,058,868 A | 10/1991 | Sirven |
| 5,061,541 A | 10/1991 | Gertel |
| 5,062,012 A | 10/1991 | Maeda et al. |
| 5,068,749 A | 11/1991 | Patel |
| 5,069,527 A | 12/1991 | Johnson, Jr. et al. |
| 5,071,108 A | 12/1991 | Houghton, Jr. |
| 5,074,021 A | 12/1991 | Feng et al. |
| 5,077,747 A | 12/1991 | Hemmer et al. |
| RE33,937 E | 5/1992 | Schubert |
| 5,116,190 A | 5/1992 | Silke |
| 5,132,824 A | 7/1992 | Patel et al. |
| 5,138,496 A | 8/1992 | Pong |
| 5,140,470 A | 8/1992 | Luecke |
| 5,146,532 A | 9/1992 | Hodge |
| 5,150,236 A | 9/1992 | Patel |
| 5,154,963 A | 10/1992 | Terry |
| 5,168,168 A | 12/1992 | Luecke |
| 5,170,104 A | 12/1992 | Laughlin |
| 5,172,160 A | 12/1992 | Van Eijk et al. |
| 5,179,618 A | 1/1993 | Anton |
| 5,183,350 A | 2/1993 | Kramer |
| 5,189,725 A | 2/1993 | Bensel, III et al. |
| 5,191,587 A | 3/1993 | Hanson et al. |
| 5,194,993 A | 3/1993 | Bedzyk |
| 5,195,157 A | 3/1993 | Penfold |
| 5,214,735 A | 5/1993 | Henneberger et al. |
| 5,218,258 A | 6/1993 | Shirasu et al. |
| 5,218,610 A | 6/1993 | Dixon |
| 5,219,051 A | 6/1993 | Davis |
| 5,245,552 A | 9/1993 | Andersson et al. |
| 5,251,863 A | 10/1993 | Gossman et al. |
| 5,281,812 A | 1/1994 | Lee et al. |
| 5,285,995 A | 2/1994 | Gonzalez et al. |
| 5,289,559 A | 2/1994 | Wilson |
| 5,300,755 A | 4/1994 | Nishitani et al. |
| 5,311,278 A | 5/1994 | Rosencher |
| 5,319,435 A | 6/1994 | Melle et al. |
| 5,321,539 A | 6/1994 | Hirabayashi et al. |
| 5,327,061 A | 7/1994 | Gullapalli |
| 5,337,383 A | 8/1994 | DeAngelis et al. |
| 5,340,371 A | 8/1994 | Dyott |
| 5,367,140 A | 11/1994 | Jonaneh et al. |
| 5,379,980 A | 1/1995 | Houghton, Jr. et al. |
| 5,410,145 A | 4/1995 | Coroy |

| | | |
|---|---|---|
| 5,412,991 A | 5/1995 | Hobbs |
| 5,428,225 A | 6/1995 | Silva et al. |
| 5,428,635 A | 6/1995 | Zhiglinsky et al. |
| 5,434,790 A | 7/1995 | Saka et al. |
| 5,434,944 A | 7/1995 | Kerry et al. |
| 5,434,945 A | 7/1995 | Burek et al. |
| 5,442,167 A | 8/1995 | Cornelius et al. |
| 5,446,519 A | 8/1995 | Makinouchi |
| 5,463,647 A | 10/1995 | Pan |
| 5,469,265 A | 11/1995 | Measures et al. |
| 5,483,055 A | 1/1996 | Thompson et al. |
| 5,499,261 A | 3/1996 | Welch et al. |
| 5,500,269 A | 3/1996 | Terry |
| 5,502,598 A | 3/1996 | Kimura et al. |
| 5,510,603 A | 4/1996 | Hess et al. |
| 5,517,857 A | 5/1996 | Hobbs |
| 5,528,718 A | 6/1996 | Ray et al. |
| 5,530,547 A | 6/1996 | Arnold |
| 5,530,785 A | 6/1996 | Sakamoto et al. |
| 5,553,186 A | 9/1996 | Allen |
| 5,563,972 A | 10/1996 | Krausse et al. |
| 5,564,537 A | 10/1996 | Shoureshi |
| 5,570,444 A | 10/1996 | Janssen et al. |
| 5,581,077 A | 12/1996 | Chirovsky et al. |
| 5,598,500 A | 1/1997 | Crespel et al. |
| 5,603,387 A | 2/1997 | Beard et al. |
| 5,617,501 A | 4/1997 | Miller et al. |
| 5,619,609 A | 4/1997 | Pan et al. |
| 5,626,157 A | 5/1997 | Galpin et al. |
| 5,638,267 A | 6/1997 | Singhose et al. |
| 5,638,482 A | 6/1997 | Winterhoff et al. |
| 5,653,317 A | 8/1997 | Wakui |
| 5,653,894 A | 8/1997 | Ibbotson et al. |
| 5,654,903 A | 8/1997 | Reitman et al. |
| 5,655,045 A | 8/1997 | Morlion et al. |
| 5,660,255 A | 8/1997 | Schubert et al. |
| 5,668,906 A | 9/1997 | Yamamura et al. |
| 5,673,350 A | 9/1997 | Song et al. |
| 5,689,607 A | 11/1997 | Vincent et al. |
| 5,695,331 A | 12/1997 | Nutter et al. |
| 5,705,802 A | 1/1998 | Bobba et al. |
| 5,717,804 A | 2/1998 | Pan et al. |
| 5,725,066 A | 3/1998 | Beard et al. |
| 5,737,132 A | 4/1998 | Luecke et al. |
| 5,745,633 A | 4/1998 | Giebel et al. |
| 5,745,987 A | 5/1998 | Bartley et al. |
| 5,748,821 A | 5/1998 | Schempp et al. |
| 5,751,877 A | 5/1998 | Ishizaka et al. |
| 5,757,561 A | 5/1998 | Sechrist et al. |
| 5,758,004 A | 5/1998 | Alarcon et al. |
| 5,761,360 A | 6/1998 | Grois et al. |
| 5,764,678 A | 6/1998 | Tada |
| 5,765,800 A | 6/1998 | Watanabe et al. |
| 5,768,768 A | 6/1998 | Best |
| 5,774,614 A | 6/1998 | Gilliland et al. |
| 5,779,010 A | 7/1998 | Nelson |
| 5,791,621 A | 8/1998 | Yashima |
| 5,793,920 A | 8/1998 | Wilkins et al. |
| 5,793,921 A | 8/1998 | Wilkins et al. |
| 5,794,912 A | 8/1998 | Whittaker et al. |
| 5,795,912 A | 8/1998 | Tsubota |
| 5,812,958 A | 9/1998 | Mayama |
| 5,823,307 A | 10/1998 | Schubert et al. |
| 5,825,558 A | 10/1998 | Farmiga et al. |
| 5,852,519 A | 12/1998 | Do et al. |
| 5,857,049 A | 1/1999 | Beranek et al. |
| 5,880,461 A | 3/1999 | Spear |
| 5,880,465 A | 3/1999 | Boettner et al. |
| 5,880,894 A | 3/1999 | Blakley |
| 5,884,736 A | 3/1999 | Burdisso et al. |
| 5,909,324 A | 6/1999 | Bryant et al. |
| 5,912,442 A | 6/1999 | Nye et al. |
| 5,930,057 A | 7/1999 | Sechrist et al. |
| 5,931,441 A * | 8/1999 | Sakamoto .................... 248/550 |
| 5,941,508 A | 8/1999 | Murata et al. |
| 5,941,920 A | 8/1999 | Schubert |
| 5,946,023 A | 8/1999 | Blanding |
| 5,962,104 A | 10/1999 | Gertel et al. |
| 5,963,695 A | 10/1999 | Joyce |
| 5,969,256 A | 10/1999 | Hobbs |
| 6,014,206 A | 1/2000 | Basting et al. |
| 6,016,230 A | 1/2000 | Nunnally et al. |
| 6,022,005 A | 2/2000 | Gran et al. |
| 6,026,550 A | 2/2000 | Silano |
| 6,036,162 A | 3/2000 | Hayashi |
| 6,056,447 A | 5/2000 | Caras |
| 6,078,845 A | 6/2000 | Friedman |
| 6,087,621 A | 7/2000 | Kang et al. |
| 6,184,987 B1 | 2/2001 | Jang et al. |
| 6,196,514 B1 * | 3/2001 | Kienholz ...................... 248/550 |
| 6,198,580 B1 | 3/2001 | Dallakian |
| 6,202,492 B1 | 3/2001 | Ohsaki |
| 6,209,841 B1 * | 4/2001 | Houghton et al. ............ 248/550 |
| 6,212,759 B1 | 4/2001 | Liu et al. |
| 6,213,442 B1 | 4/2001 | Ivers et al. |
| 6,220,100 B1 | 4/2001 | Felkins et al. |
| 6,222,665 B1 | 4/2001 | Neuner et al. |
| 6,240,398 B1 | 5/2001 | Allen et al. |
| 6,241,435 B1 | 6/2001 | Huang et al. |
| 6,254,069 B1 * | 7/2001 | Muramatsu et al. ..... 267/140.14 |
| 6,286,644 B1 | 9/2001 | Wakui |
| 6,304,393 B1 | 10/2001 | Sechrist et al. |
| 6,311,478 B1 | 11/2001 | Elorriaga Vicario et al. |
| 6,317,278 B1 | 11/2001 | Metsala |
| 6,390,887 B1 | 5/2002 | Ulloa |
| 6,394,407 B1 * | 5/2002 | Ryaboy ......................... 248/638 |
| 6,417,976 B1 | 7/2002 | Schuster et al. |
| 6,441,895 B1 | 8/2002 | Kogan et al. |
| 6,474,712 B1 | 11/2002 | Govzman et al. |
| 6,490,025 B1 | 12/2002 | Makinouchi et al. |
| 6,511,035 B1 * | 1/2003 | Teel et al. ..................... 248/550 |
| 6,619,611 B2 * | 9/2003 | Ryaboy et al. ................ 248/631 |
| 6,626,411 B2 * | 9/2003 | Houghton et al. ............ 248/550 |
| 6,648,295 B2 * | 11/2003 | Herren et al. ................. 248/636 |
| 6,700,304 B1 | 3/2004 | Fuller et al. |
| 6,758,313 B2 * | 7/2004 | Binnard ........................ 188/378 |
| 7,320,455 B2 | 1/2008 | Ryaboy et al. |
| 2001/0022793 A1 | 9/2001 | Yokoyama |
| 2002/0145102 A1 | 10/2002 | Eckelkamp-Baker et al. |
| 2002/0186508 A1 | 12/2002 | Kube et al. |
| 2005/0109914 A1 | 5/2005 | Ryaboy et al. |
| 2006/0086293 A1 | 4/2006 | Ryaboy et al. |
| 2008/0121779 A1 | 5/2008 | Ryaboy |

FOREIGN PATENT DOCUMENTS

| | | |
|---|---|---|
| GB | 2 124 402 A | 7/1982 |
| GB | 2 131 971 A | 6/1984 |
| JP | 03021894 | 1/1991 |
| JP | 6-33981 | 2/1994 |
| JP | 08088167 | 9/1994 |
| JP | 09330875 | 6/1996 |
| JP | 10144601 | 11/1996 |
| WO | WO9607118 | 3/1996 |

OTHER PUBLICATIONS

P. Zorabedian and W. R. Trutna, Jr., "Interference-filter-tuned, alignment-stabilized, semiconductor external-cavity laser", 1988, Optical Society of America.

A. Schremer and C. L. Tang. "Single-Frequency tunable external-cavity semiconductor laser using an electro-optic birefringent modulator", Appl. Phys. Lett., vol. 55, No. 1, Jul. 3, 1989.

M. W. Maeda, J. S. Patel, D. A. Smith, Chinlon Lin, M. A. Saifi, and A. Von Lehman, "An Electronically Tunable Fiber Laser with a Liquid-Crystal Etalon Filter as the Wavelength-Tuning Element", IEEE Photonics Technology Letters, vol. 2, No. 11, Nov. 1990.

Katsuhiko Hirabayashi, Hiroyuki Tsuda, and Takashi Kurokawa, "Tunable Liquid-Crystal Fabry-Perol Interferometer Filter for Wavelength-Division Multiplexing Communication Systems", Journal of Lightwave Technology, vol. 11, No. 12, Dec. 1993.

Stephen R. Mallinson, "Wavelength-selective filters for single-mode fiber WDM systems using Fabry-Perot interferometers", Applied Optics, vol. 26, No. 3, Feb. 1, 1987.

W. Gunning, J. Pasko, J. Tracy, "A liquid crystal tunable spectral filter: visible and infrared operation", SPIE vol. 268 Imaging Spectroscopy (1981).

Hiroyuki Tsuda, Katsuhiko Hirabayashi, Yuichi Tohmori, and Takashi Kurokawa, "Tunable Light Source Using a Liquid-Crystal Fabry-Perot Interferometer", IEEE Photonics Technology Letters, vol. 3. No. 6, Jun. 1991.

John R. Andrews, "Low Voltage Wavelength Tuning of an External Cavity Diode Laser Using a Nematic Liquid Crystal-Containing Birefringent Filert", IEEE Photonics Technology Letters, vol. 2, No. 5, May 1990.

N. A. Olsson and J. P. Van Der Ziel, "Performance Characteristics of 1.5-um External Cavity Semiconductor Lasers for Coherent Optical Communication", Journal of Lightwave Technology, vol. LT-5, No. 4, Apr. 1987.

Hecht Optics Second Edition, Eugene Hecht, reprinted 1990, reference text, pp. 303 # 368.

Rivin, Eugene I., "Vibration isolation of precision equipment", Precision Engineering, 1995, pp. 41-56, vol. 17.

Marsh Mellow Springs Vibration isolation Design Manual, 1998, Firestone Industrial Products Company.

Rivin, Eugene I., "Shaped Elastomeric Components for Vibration Control Devices", Sound and Vibration, Jul. 1999, pp. 18-23, vol. 33, No. 7.

Grafstrom, S. et al., "Fast Laser Beam Position Control with Submicroradian Precision," Optics Communications, Jan. 1988, vol. 65, No. 2.

Newport Corporation, "The Newport Resource" catalog, 2003, pp. 1176-1177; 1215-1219.

C.M. Harris, "Shock and Vibration Handbook", 4th edition, 1996; 5th edition, 2001, Ch. 37.

Office Action mailed on: Mar. 18, 2005 for U.S. Appl. No. 10/693,222, filed Oct. 24, 2003 and issued as 7,320,455 on Jan. 22, 2008.

Office Action mailed on: Sep. 13, 2005 for U.S. Appl. No. 10/693,222, filed Oct. 24, 2003 and issued as 7,320,455 on Jan. 22, 2008.

Office Action mailed on: May 30, 2006 for U.S. Appl. No. 10/693,222, filed Oct. 24, 2003 and issued as 7,320,455 on Jan. 22, 2008.

Office Action mailed on: May 16, 2007 for U.S. Appl. No. 10/693,222, filed Oct. 24, 2003 and issued as 7,320,455 on Jan. 22, 2008.

Office Action mailed on: Oct. 26, 2007 for U.S. Appl. No. 10/693,222, filed Oct. 24, 2003 and issued as 7,320,455 on Jan. 22, 2008.

Office Action mailed on: Jan. 18, 2007 for U.S. Appl. No. 10/971,623, filed Oct. 22, 2004 and published as 2006/0086293-A1 on Apr. 27, 2006.

Office Action mailed on: May 1, 2008 for U.S. Appl. No. 10/971,623, filed Oct. 22, 2004 and published as 2006/0086293-A1 on Apr. 27, 2006.

Office Action mailed on: Apr. 15, 2009 for U.S. Appl. No. 10/971,623, filed Oct. 22, 2004 and published as 2006/0086293-A1 on Apr. 27, 2006.

Office Action mailed on: Jun. 1, 2009 for U.S. Appl. No. 10/971,623, filed Oct. 22, 2004 and published as 2006/0086293-A1 on Apr. 27, 2006.

* cited by examiner

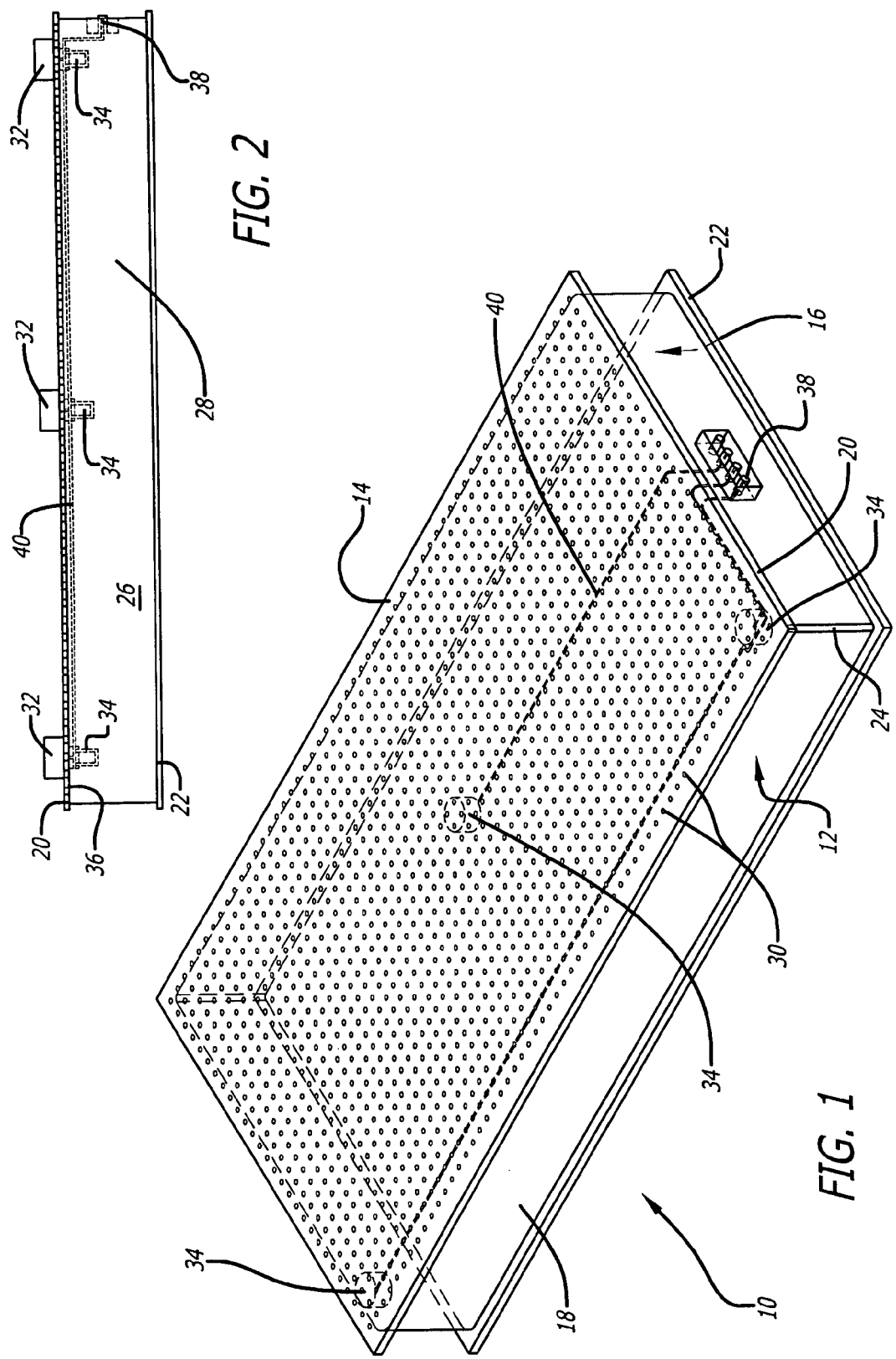

METHODS AND DEVICES FOR ACTIVE VIBRATION DAMPING OF AN OPTICAL STRUCTURE

CROSS REFERENCE TO RELATED APPLICATIONS

This application claims priority under 35 U.S.C. section 119(e) from copending U.S. Provisional Patent Application Ser. No. 60/634,227, entitled "Method and Apparatus for Active Vibration Dampening of an Optical Structure or Substrate", filed Dec. 7, 2004, by V. Ryaboy, P. Kasturi and A. Nastase, which is hereby incorporated by reference herein in its entirety. This application is related to commonly owned co-pending U.S. patent application Ser. No. 10/693,222, entitled "Instrumented Platform for Vibration-Sensitive Equipment" filed Oct. 24, 2003, by Ryaboy et al., and commonly owned co-pending U.S. patent application Ser. No. 10/971,623, entitled "Instrumented Platform for Vibration Sensitive Equipment", filed Oct. 22, 2004, by Ryaboy et al., both of which are incorporated by reference herein in their entirety.

BACKGROUND

In many experimental research and industrial applications equipment and methods are used that are adversely affected by vibration. Vibration may be intrinsically caused by the equipment and methods, or the vibration may be transferred to the equipment from the surrounding environment. As such, it is desirable in these circumstances to have a low vibration mount surface and mount components for mounting such sensitive equipment. One example of an optical structure with an optical mount surface is an optical table which is typically used for mounting optical equipment as well as other equipment that is sensitive to vibration. In order to reduce vibration transferred to an optical table, most optical tables are equipped with vibration isolators which reduce vibration transmitted to the table from the floor upon which the table rests.

The vibration isolators may be assembled to the table at predetermined locations to optimize damping of the vibrational modes of the optical table. Often, one or more vibration isolators are positioned between a coupling surface of the optical table and the one or more table supports or legs, thereby passively limiting the transmission of vibrational influences from the environment to the devices supported on the coupling surface of the table. Exemplary passive vibration isolators include fluid bladders, springs, shocks, foams, and the like.

An optical table itself, however, has its own natural frequencies and corresponding flexural vibration modes that can be easily excited by residual vibration coming through the isolators or by other sources such as acoustical excitation, air turbulence and dynamic forces generated by the payload equipment installed on the optical table. The main flexural vibration modes usually have a global character, which means that an excitation at any point of the table generates a vibration pattern encompassing the whole optical table structure. These natural vibrations are only very lightly damped, in general, and therefore can reach high amplitudes unless special damping means are introduced into the optical table structure. Some special damping means may include passive dampers that may be specifically tailored to natural frequencies of the optical table.

Passive dampers of various designs are widely used in construction of optical tables. The "Shock and Vibration Handbook", ed. By C. M. Harris, 4$^{th}$ edition, 1996; 5$^{th}$ edition, 2001, Ch. 37, provides a survey and a classification of dampers or damping treatments. According to this reference, known types of damping treatments include free-layer damping treatments, where the energy is dissipated by means of extensional deformation of a damping layer (made of visco-elastic material) induced by flexural vibration of the base structure. Also included are constrained-layer damping treatments, where the constraining layer helps induce relatively large shear deformations in the visco-elastic layer in response to flexural vibration of the base structure, thereby providing more effective energy dissipation mechanism. Also included are integral damping treatments, including use of damped laminated sheets and/or damped joints in the construction assembly and tuned passive dampers, which are essentially mass-spring systems having resonances which are matched or tuned to one or more resonance frequencies of the base structure. The application of the tuned damper replaces the resonance peak of the base structure, typically, by two peaks of lesser amplitude. Finally, damping links, i.e., visco-elastic elements joining two parts of the structure that experience large relative motion in the process of vibration are disclosed.

However, even with such passive damping equipment installed, an optical table or other optical structure may have vibration characteristics different than an analytical model that was used to tune such damping equipment. Additionally, differing payload configurations may create differing harmonic frequencies as well as differing nodes and anti-nodes in an optical table or other optical structure. Also, there is a growing demand for high precision and high throughput capabilities in the optoelectronics and semiconductor industries, as well as similar needs for modern scientific experimental instruments. These needs require higher damping performance of optical structures such as optical tables and optical components that may be mounted to optical mount surfaces of the optical tables.

In light of the foregoing, there is an ongoing need for methods and devices configured to efficiently reduce vibration in an optical structure that arise from a variety of vibration sources. In addition, there is a need for vibration damping capability that may be moved about an optical mount surface of an optical structure such as an optical table or the like in order to position the damping capability in the location where it is needed most. What has also been needed are systems and methods for applying vibration damping capability directly to optical components which may be mounted onto an optical mount surface of an optical structure. Also, there is a need for control systems for active vibration damper assemblies that are adaptable to payload changes on an optical structure, can accommodate a wide variety of vibration magnitude variations, can be easily or automatically tuned and can be incorporated into active vibration damping systems which may be produced at a modest cost.

SUMMARY

In one embodiment, a method of adaptively tuning a controller of an active vibration damper system includes providing an active vibration damper system for an optical structure including at least one active vibration damper assembly. The vibration damper assembly has a vibration sensor and an actuator. The damper system includes a controller coupled to both the sensor and the actuator by a control channel. Initially, all control channels except one active channel are disabled. In the remaining active control channel, the gain factor of the control channel is increased until instability of the active damper system is detected by the vibration sensor. The gain factor is then reduced by a small increment to re-achieve stability of the active damper system. The gain factor that achieved stability is then stored. The procedure is then repeated for any remaining control channels. Thereafter, all control channels are reactivated and gain factors to each control channel increased in an amount or amounts proportional to the stored gain values. The gain factors are proportionally increased for each respective channel until instability is again detected by a vibration sensor. The gain factors are then reduced in small steps for each control channel until stability is achieved for the vibration damper system.

In another embodiment, a method of automatically selecting an appropriate range of input vibration signal detection in an active damper assembly includes providing an active vibration damper system for an optical structure. The active vibration damper system includes an active vibration damper assembly having a vibration sensor and an actuator and a controller coupled to both the vibration sensor and the actuator by a control channel. The controller also has at least one vibration feedback signal input with gain factors appropriate to the signal strength range for the inputs. A vibration feedback signal from the vibration sensor is monitored. The vibration feedback signal is compared to a pre-selected range of signal values over a pre-selected period of time. An appropriate feedback signal range input is selected with an gain factor appropriate for the input signal amplitude in the controller.

In another embodiment, a method of determining a payload change applied to an active vibration damper system includes providing an active vibration damper system. The active vibration damper system provided includes an active damper assembly having a vibration sensor and an actuator and a controller coupled to both the vibration sensor and the actuator by a control channel. The controller also has a vibration feedback signal input with gain factor appropriate to the signal strength range for the vibration signal input. A vibration feedback signal is monitored for vibration overload conditions. Upon detection of a vibration overload condition, the drive signal to the actuator from the controller is disabled and a determination is made as to whether the vibration overload condition still exists. If the overload condition ceases when the drive signal to the actuator from the controller is disabled, a change in payload has occurred.

In one embodiment, an optical component with active vibration damping includes a body portion and a mount plate secured to the body portion and configured to be mounted to an optical mount surface. An actuator is mechanically coupled to the body portion. In some embodiments, a vibration sensor is also mechanically coupled to the body portion with a controller in communication with the actuator and vibration sensor. For some embodiments, the optical component may include an optical post mount.

These features of embodiments will become more apparent from the following detailed description when taken in conjunction with the accompanying exemplary drawings.

BRIEF DESCRIPTION OF THE DRAWINGS

FIG. 1 is a perspective view of a optical structure in the form of an optical table;

FIG. 2 is a side sectional view of the optical table;

DETAILED DESCRIPTION

Figure 3:
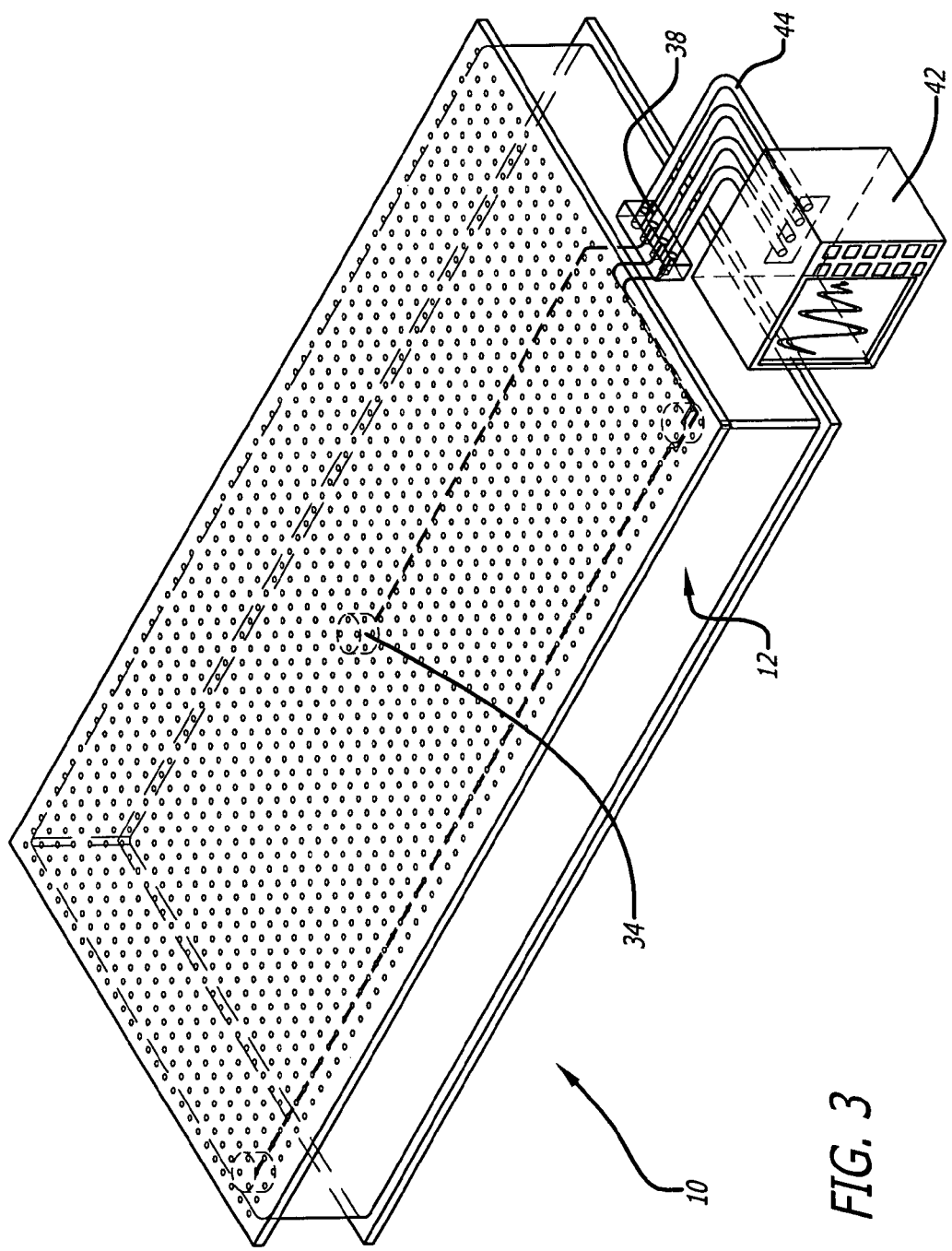
FIG. 3 is a perspective view of the optical table coupled to a monitor and/or controller.

As discussed above, in many experimental research and industrial applications equipment and methods are used that are adversely affected by vibration. Vibration may be intrinsically caused by the equipment and methods, or the vibration may be transferred to the equipment from the surrounding environment. As such, it is desirable in these circumstances to use low vibration optical structures that may include optical mount surfaces and optical components that may be mounted to optical mount surfaces. Optical mount surfaces may be found on optical structures such as optical tables, optical benches, optical breadboards, laser platforms, optical platforms and the like. Optical components may include, without limitation, optical mounts, optical posts, lens holders, lasers, adjustable platforms and the like.

Some embodiments include an active vibration damper assembly that may be detachably secured to an optical mount surface of an optical structure such as an optical table. Such embodiments may be detached and moved about a surface of an optical table or other optical mount surface to a desired location and then re-attached to the optical mount surface. Other embodiments include a vibration damper assembly that may be incorporated into an optical structure having an optical mount surface such as an optical table. The active vibration damper assembly embodiment includes at least one sensor and at least one actuator which may optionally be located or disposed within a housing. The housing of a detachable embodiment of an active damper assembly may be attached to any surface of the table or work surface. For example, in some embodiments, the vibration damper assembly is configured to be attached to an optical mount surface of an optical table or platform configured to support any number of optical components. In some embodiments, the vibration damper assembly may be coupled to an optical mount surface of an optical table adjacent to one or more optical table supports or legs. In some embodiments, the vibration damper assembly may be coupled to a surface of the optical table in opposition to the one of more optical table support structures or legs. The housing may be configured to attach to a surface of an optical table or platform using one or more fasteners. For example, in some embodiments the active vibration damper assembly may be detachably coupled to a surface of an optical table or platform. As such, an operator can move the active vibration damper assembly to different locations of the table or platform, thereby permitting the operator to optimize the damping function of the vibration damper assembly.

FIGS. 1 and 2 show an optical structure which has an optical mount surface and which is in the form of a platform 10. The platform 10 may include an optical table 12 that has a first surface 14, a second surface 16 and a plurality of side surfaces 18. The first surface 14 may extend along a first plate 20, the second surface 16 may extend along a second plate 22 and the side surfaces 18 may extend along one or more side plates 24.

The first plate 20 is separated from the second plate 22 by an inner core 26. The first plate 20 and second plate 22 of the platform 10 may be constructed of one or more materials including, without limitation, stainless steel, aluminum, carbon fiber, granite, steel, carbon steel, laminated metals, composite metals, wood, laminated woods, composite woods, formica, formica covered substrates, fiberglass, composite materials, Kevlar, cast iron, and the like. The first plate 20 and second plate 22 may be manufactured from a like material. In the alternative, the first plate 20 and second plate 22 may be manufactured from different materials.

Like the first and second plates 20, 22, the inner core 26 of the platform 10 may be manufactured from a variety of materials. Exemplary core materials include, without limitation, various metals and metallic composites including steel, titanium, aluminum, iron; granite; various woods and wood composites including medium density fiber board, particle board, and the like; cardboard, multiple component laminates; composite materials including carbon fiber, Kevlar, and the like; and similar materials. In one embodiment, the inner core 26 may contain a honeycomb structure 28 to provide support for the plates 20 and 22. Optionally, the inner core 26 may be constructed without a honeycomb structure.

Optionally, the first plate 20 and/or the second plate 22 may be configured to have any number of mounting features. For example, the first plate 20 and/or the second plate 22 may include a plurality of mounting features in the form of threaded apertures 30 which are configured to receive at least a portion of a mounting device of an optical component or the like such as a threaded bolt or screw with threads configured to mate with the threaded apertures 30. Optionally, the apertures 30 need not be threaded and the mounting of optical components or other components to be mounted to an optical mount surface may use gravitational forces, magnetic forces or the like. Exemplary optical components may include, without limitation, optical mounts, posts, lens supports, isolation supports or platforms, and the like. In other embodiments, the platform 10 may be configured to support a variety of measuring devices or other vibration-sensitive devices thereon. For example, the platform 10 may be configured to support a mass spectroscopy device, nuclear magnetic resonance (NMR) measuring device, crystal growth apparatus or similar vibration-sensitive devices thereon. In other embodiments, first plate 20 and/or the second plate 22 may be configured to have one or more optical components or similar devices magnetically coupled thereto. As such, the first plate 20, second plate 22, or both may be manufactured without apertures 30 therein. Optionally, the platform 10 may be configured to have one or more optical components or devices coupled thereto using any one of a number of attachment methodologies. Exemplary attachment methodologies include, without limitation, detachably coupled, non-detachably coupled, welded, adhesively coupled, friction coupled, electro-magnetically coupled, or the like.

Referring again to FIGS. 1 and 2, an external payload 32 that may be a vibration-sensitive payload 32 may be attached to one or more threaded apertures 30 of the table 12. The payload 32 may be any type of weight or mass including a device such as an optical component of an optical system, a device under test in a shaker machine, a mass spectroscopy device, nuclear magnetic resonance (NMR) measuring device, crystal growth apparatus etc. Additionally, the table may be a platform for equipment used to fabricate semiconductor wafers, integrated circuits, etc. In general the table 12 may be any platform used to support a component, system or equipment used in manufacturing or laboratory environments.

One or more vibration sensors 34 may be located within the inner core 26 and attached to an underlying surface 36 of the first plate 20. The vibration sensors 34 may be any type of device, such as an accelerometer, a geophone or displacement sensor that can sense vibration. Although three vibration sensors 34 are shown, it is to be understood that any number of sensors 34 can be located at any location of the table. The vibration sensors 34 can be connected to an electrical connector 38 attached to one of the side plates 24 of the table 12. The sensor 34 may be connected to the connector 38 by wire cables 40 that run through the inner core 26. The sensors 34 may provide an output signal that is transmitted to the connector 38 over the cables 40.

As shown in FIG. 3, a monitor and/or controller 42 may be coupled to the sensors 34 by plugging cables 44 into the connector 38. The monitor and/or controller 42 may record and/or display vibration information provided by the sensors 34. Optionally, the monitor and/or controller 42 may be configured to provide a control signal to an active or controllable actuator (not shown) integrated into the table 10. Referring again to FIG. 3, by locating the vibration sensors 34 within the inner core 26, the sensors 34 can measure the vibration directly beneath the external device 32 thereby providing more accurate vibration data. The electrical connector 38 allows the controller 42 to be readily coupled to the sensors 34 thereby minimizing set-up time for monitoring vibration in the table 12. Although cables 40 and a connector 38 are shown and described, it is to be understood that the sensors 34 may have a wireless transmitter (not shown) that wirelessly transmits an output signal or signals from the sensors 34 to the monitor and/or controller 42.

Figure 4:
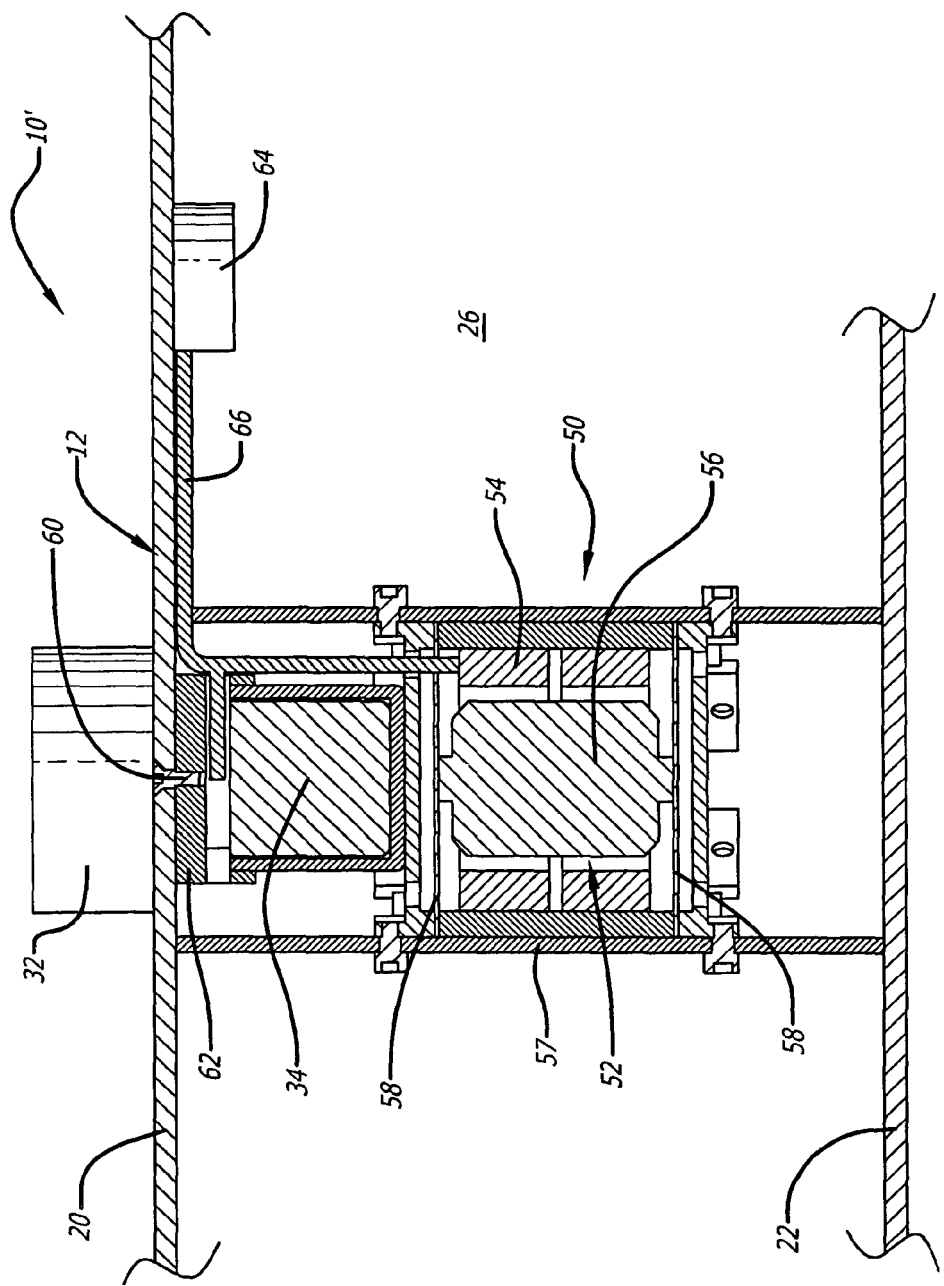
FIG. 4 is a cross-sectional view of a portion of an embodiment of an optical table with an active damper assembly in a table core.

FIG. 4 shows an embodiment of a table assembly 10' with a vibration damper assembly 50 located within the inner core 26. The active or controllable vibration damper assembly 50 may include the sensor 34 and an actuator 52 having an active element 54 in the form of an electric coil such as a voice coil that can be excited to induce a vibration that offsets and cancels the vibration of an optical structure such as the table 12. The electric coil of the actuator 52 is magnetically coupled to a magnet mass 56. The magnet mass 56 is mechanically coupled to an actuator housing 57 by flexures in the form of a pair of flexible diaphragms 58. The housing 57 is attached to the plates 20 and 22. That diaphragms 58 function as springs which combine with the mass 56 to form a spring/mass assembly. Providing a current to the coil 54 generates a magnetic force that moves the mass 56. The coil 54 can be excited in a manner to generate, together with the spring/mass assembly, a dynamic force to offset vibration in the table 12.

Figure 5:
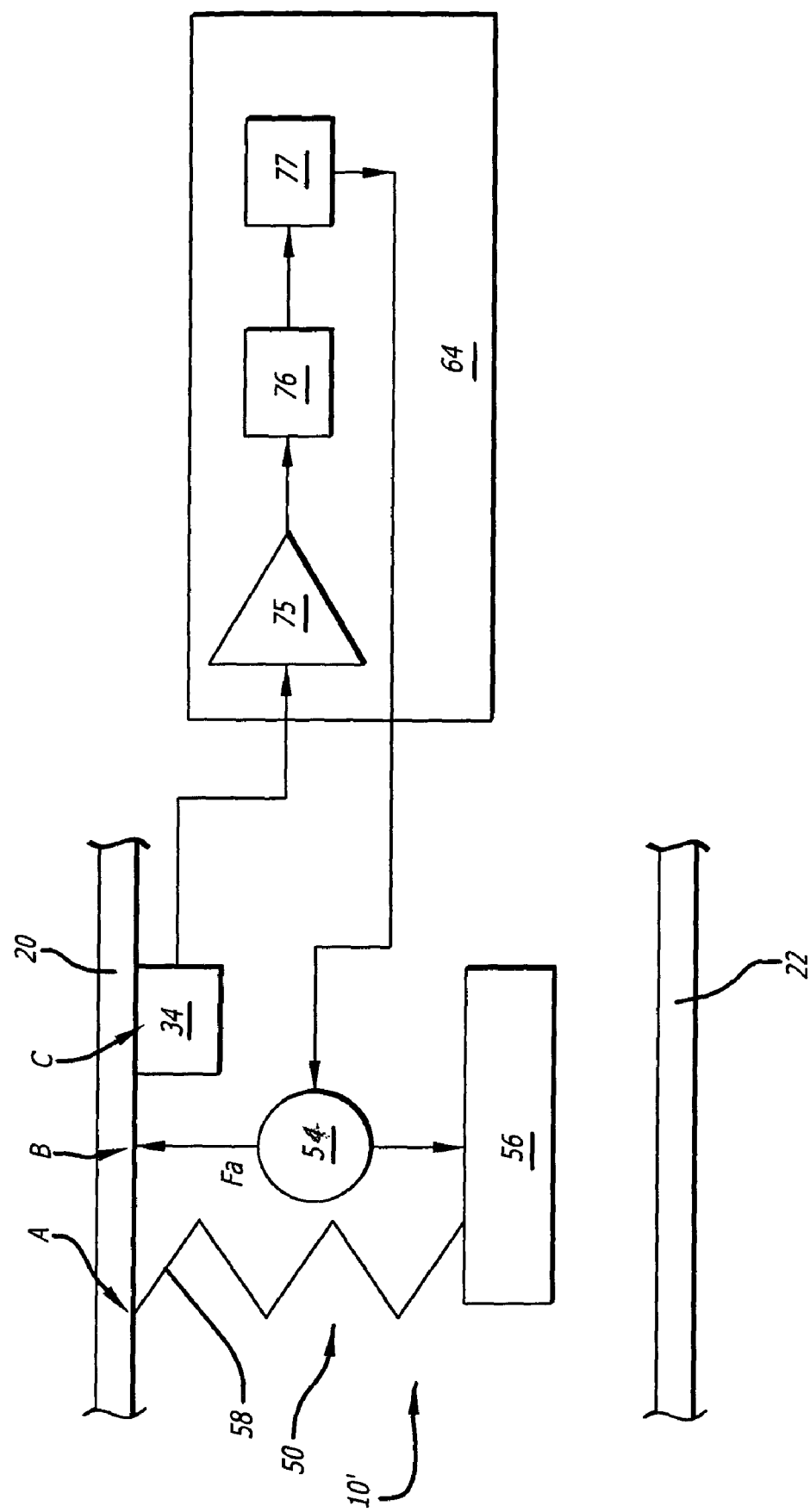
FIG. 5 is a schematic of an active vibration damper system including an active or controllable vibration damper assembly in an optical table core.

The vibration sensor 34 may be coupled to the optical table 12 using a variety of techniques. For example, the vibration sensor 34 may be coupled to the table using a screw 60 that extends through the top plate 20 and is attached to a sensor housing 62. The sensor 34 may be coaxial and rigidly coupled to the actuator 52. The sensor 34 provides an output signal to a control circuit 64 as shown in FIG. 5. The control circuit 64 processes the output signal and provides an excitation signal to the coil 54 to generate an offsetting vibration that cancels the table vibration. The control circuit 64 can be located within the inner core 26 and connected to the sensor 60 and coil 54 by cables 66.

While certain exemplary embodiments have been described and shown, it is to be understood that such embodiments are merely illustrative of and not restrictive and various other modifications may be used. In particular, optical structures referred to as optical tables or optical mount surfaces thereof may include any kind of a support structure, including multi-level platforms or cradle platforms. The working or optical mount surface of these support structures may be horizontal, vertical or even inclined. Accordingly, the line of action of the sensors and active dampers can be vertical, horizontal or inclined and multidirectional sensor or active damper embodiments are also contemplated. Although FIG. 4 shows an actuator 52 that is implemented as an electromagnetic shaker with a moving magnet 56 and a stationary coil 54, other types of actuator designs can be used, in particular, electromagnetic designs with stationary magnets and moving coils, electrodynamic designs with one stationary and one moving coil, etc. Alternatively, stiff (e.g. piezoelectric) actuators can be employed to create a relative motion of the reactive mass and the table.

Active damper assemblies are typically located at fixed positions, normally at the corners of an optical table or the like. This arrangement allows for effective reduction of natural vibrations of the table at its resonance frequencies. It may not, however, be effective for reducing forced vibration of the table caused by mechanical or acoustical excitation at a fixed frequency. Even if programmed to create increased mechanical impedance at this frequency, they may reduce vibration only locally at the installation point. In order to address this, add-on or detachable controlled vibration damper assembly embodiments may be installed near the most vibration-sensitive components or near the sources of forced vibration and programmed to reduce vibration at certain fixed frequencies, thereby providing protection against forced vibrations.

FIG. 5 is a schematic view of an active or controllable vibration damper assembly 50 coupled to a controller 64. A vibration sensor 34 of the vibration damper assembly 50 is integrated into or otherwise mechanically coupled to the table 10'. A signal from the vibration sensor 34 is transmitted to the controller 64. The controller 64 may contain amplifiers 75, compensators 76 and filters 77 as well as other components such as a processor (not shown). Digital control, analog control or both may be used to analyze the signal from the vibration sensors 34 and generate a vibration canceling output signal transmitted to the damper assembly 50. The transformed vibration canceling output signal is fed into the active element 54, such as a coil, of the actuator 52 which may be incorporated into or otherwise mechanically coupled to the table structure. The vibration actuator coil 54 may further be coupled to the reaction mass 56, which may contain magnets, and the flexure 58 that provides elastic coupling between the mass 56 and the tabletop. The amplification gains and other parameters of the controller modules of the controller 64 are assigned and coordinated with the characteristics of the sensor, actuator and mechanical assembly so that a force $F_a$ induced on the table reduces the vibration at this point. As control current flows through the coil 54 of the actuator 52, the electromagnetic force acts on the reaction mass 56, and the equivalent reaction force is acting on the stationary coils or flexure 58 fastened to the table structure. The control loop of the controller 64 is designed so that the phase and the amplitude of the summary force transmitted to the table structure counteract the vibration of the table 10' as measured by the sensor 34.

In one embodiment, the locations represented by points A, B and C in FIG. 5 may be co-axial and disposed on the same vertical axis and rigidly connected. Optionally, the control loop coupled between sensor 34 and actuator 52 of the active damper assembly 50 may be designed such that the active force acting on the table 10' emulates the effect of a viscous damper in the frequency domain encompassing the main natural frequencies of the flexural vibration of the table. This approach creates inherent stability and robustness with respect to the changes in the payload 32. To implement this strategy, an embodiment of the transfer function of the controller 64 may be designed as:

$$K(\omega) = \frac{-i\omega k}{A(\omega)S(\omega)}$$

Where;
$\omega = 2\pi f$ = a circular frequency.
$A(\omega)$ = the actuator (shaker) transfer function, or ratio of the total force N exerted by the actuator on the structure to input voltage, N/V.
$S(\omega)$ = the sensor transfer function, or the ratio of the sensor output voltage to the dynamic displacement, V/m.
$K(\omega)$ = the controller transfer function, V/V.
k = an adjustable gain.

As a result, the force exerted by the active vibration damper assembly 50 on the table structure will equal $i\omega k\mu$, where $\mu$ is the dynamic displacement amplitude of the table 10', which is equivalent to the action of the viscous damping. Of course, other units can be used. The sensor 34 may be an accelerometer, a velocimeter (such as a geophone) or a displacement sensor. Additional correcting filters may be used to improve the stability margins or other parameters.

Figure 6:
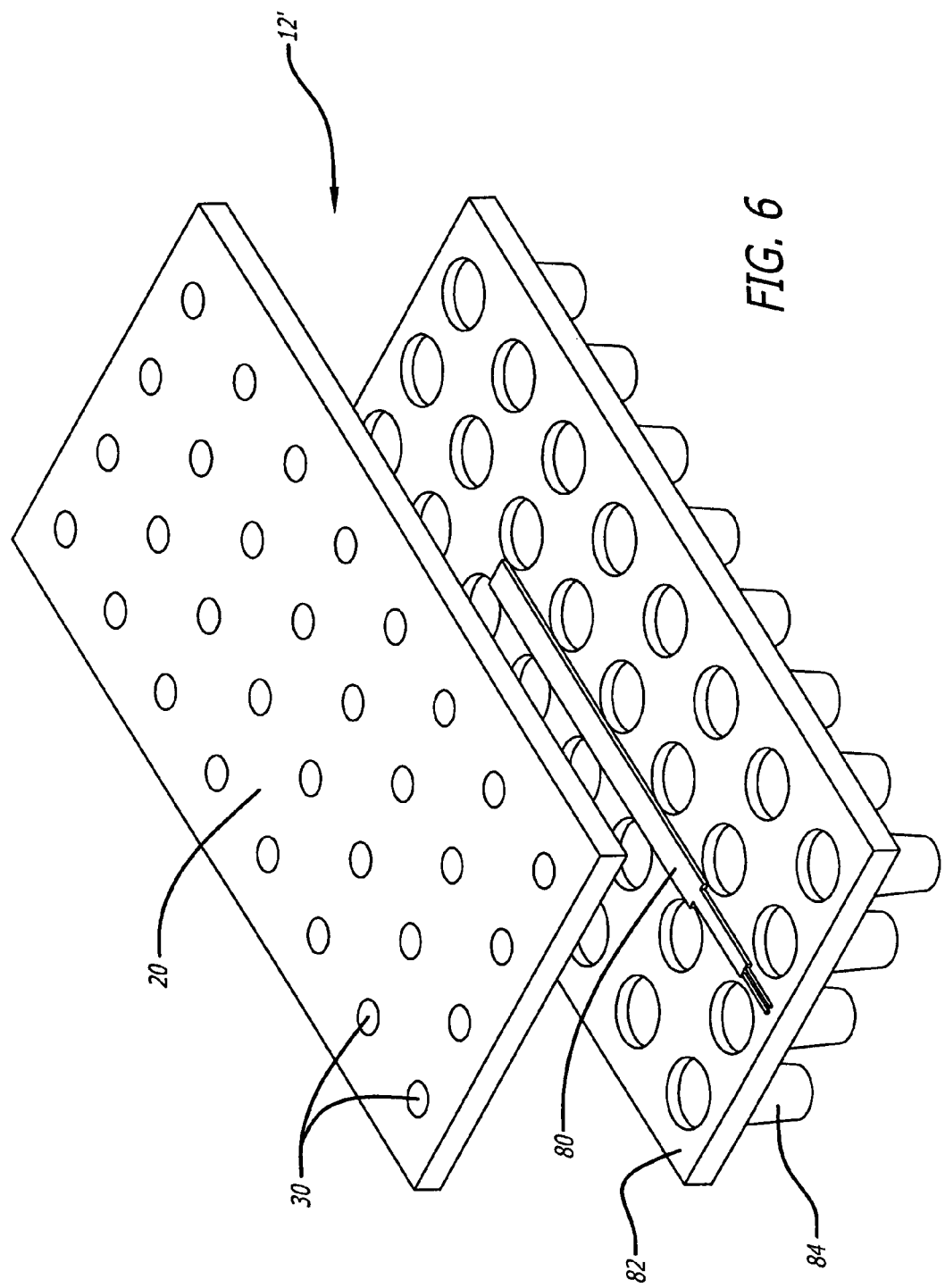
FIG. 6 is a perspective view of an embodiment of a piezoelectric active damper assembly.

FIG. 6 shows an alternate embodiment of a portion of an optical table 12 wherein a strip 80 is located between the top plate 20 and a hole sealing tile 82. The hole sealing tile 82 may have a plurality of cups 84 that are located adjacent to the threaded apertures 30 to collect debris that fall through the apertures 30. The strip 80 may be a piezoelectric device that functions as an active damper assembly with a sensor and/or an actuator such as actuator 52 discussed above. Alternatively, optical cables or other devices may be located between the plate 20 and tile 82 to provide sensing and/or actuating functions. The tile 82 can protect the strip 80 during the manufacturing process of constructing the table 12.

Figure 7:
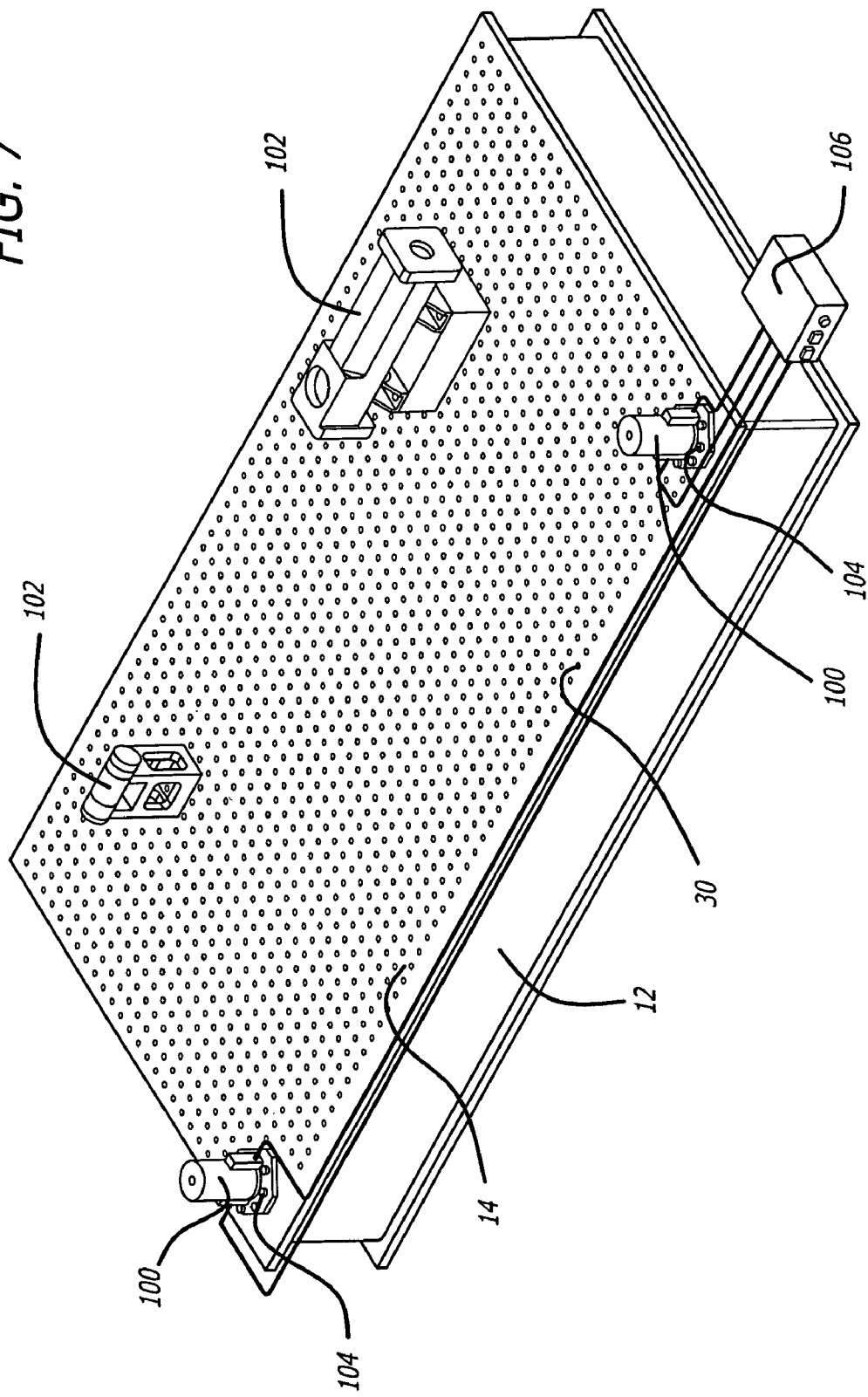
FIG. 7 is a perspective view showing an active vibration damper system attached to a payload surface of an optical table embodiment.

FIG. 7 shows a pair of vibration damper assemblies 100 that are attached to the first payload surface 14 of the table 12. The payload surface 14 may support a payload such as a pair of optical components or devices 102. Each damper assembly 100 can be attached to different locations of the payload surface 14 using various device and/or methods. For example, in one embodiment, each damper assembly 100 is secured to the table 12 by fasteners 104 screwed into the threaded apertures 30 of the table 12. Optionally, each damper assembly 100 may be coupled to the table 12 using any variety of alternative coupling techniques. Exemplary alternate coupling techniques include, without limitation, welding, adhesively bonding, magnetically coupling, clamping, and the like. As such, the damper assembly 100 may be detachably or non-detachably coupled to the table 12. When detachably coupled to the table 12, the operator of the table 12 can detach and move each damper assembly 100 to a different location of the payload surface 14 to optimize the damping function of the vibration damper assemblies 100.

The damper assemblies 100 are also coupled or connected to a controller 106. The controller 106 may be the same or similar to the controller 64 shown in FIG. 5 and described in the accompanying text. Although an external controller 106 is shown and described, it is to be understood that at least one of the assemblies 100 may be modified to contain one or more circuits of the controller 106.

Figure 8:
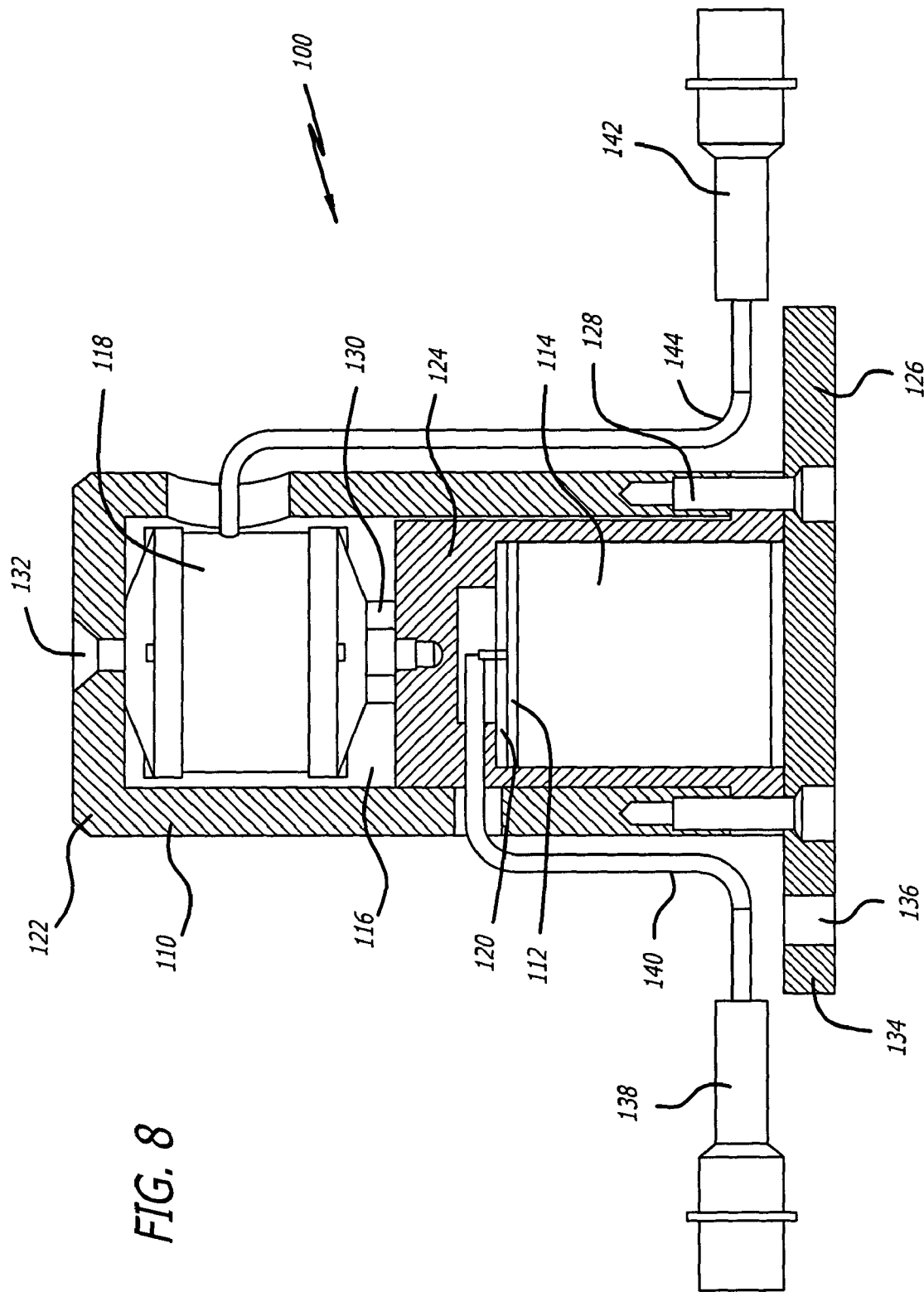
FIG. 8 is a cross-sectional view of an embodiment of a vibration damper assembly.

FIG. 8 shows an embodiment of the vibration damper assembly 100 in partial section. The assembly 100 includes a housing 110. The housing 110 may include a first compartment 112 that contains a vibration sensor 114 and a second compartment 116 that contains an actuator 118 which includes an active element, a spring member or flexure and a mass. The sensor 114 and actuator 118 may be the same as or similar to the sensor 34 and actuator 52 including active element 54, spring member diaphragm 58 and magnetic mass 56 shown in FIG. 4 and described in the accompanying text. For example, the actuator 118 may include one or more active elements. The first compartment 112 may be sealed by an O-ring 120 or other type of seal.

The housing 110 may be constructed from a metal material, such as a magnetic metal material, to isolate the sensor 114 from electromagnetic noise, particularly noise produced by the actuator 118. The housing 110 may actually be constructed from an outer shell 122, an inner shell 124 and a base 126. The housing components 122, 124 and 126 may be attached together by a plurality of fasteners 128. The actuator 118 may be coupled to the inner shell 124 by a threaded adapter 130 and held in place by fastener 132.

The base 126 may have an interface plate in the form of a collar 134 with a plurality of apertures 136 that provide thru holes for fasteners (see FIG. 7) that attach the vibration damper assembly 100 to a table or other optical structure. Although thru holes are shown and described, it is to be understood that other means may be employed to attach the vibration damper assembly 100 to the table. For example, the base 126 may have a plurality of studs that extend from the interface plate 134 and can be pressed into the apertures 30 of the table. The damper assembly 100 may include a first electrical connector 138 that is attached to the sensor 114 by a wire(s) 140 and a second electrical connector 142 that is connected to the actuator 118 by a wire(s) 144. The connectors 138 and 142 can be connected to the electrical circuits of the controller 106 shown in FIG. 7.

In operation, a vibration damper assembly 100 is attached to the payload surface 14 by inserting the fasteners 104 through the interface plate apertures 136 and securing the housing 110 to the table 12. The connectors 138 and 142 are connected to the controller 106, although the connectors 138 and 142 may be connected before attachment of the housing 110 to the table 12 or at any other suitable time. Once set up, the vibration sensor 114 senses vibration of the table surface and generates a signal which is communicated to the controller 106. The controller 106 processes the signal and generates a drive signal which is communicated to the actuator 118. The actuator 118 then converts the drive signal into vibrational motion of the mass of the actuator 118 where such vibrational motions is configured to damp the vibration of the table. An operator can attach a display or monitor (see FIG. 3) to the vibration damper assembly 100 to utilize the sensor 114 to sense and graphically display vibration at the table location. The operator can move the vibration damper assembly 100 around the table surface or any other optical mount surface to sense vibration at different locations of the payload surface 14 and to optimize damping of the table 12.

Figure 9:
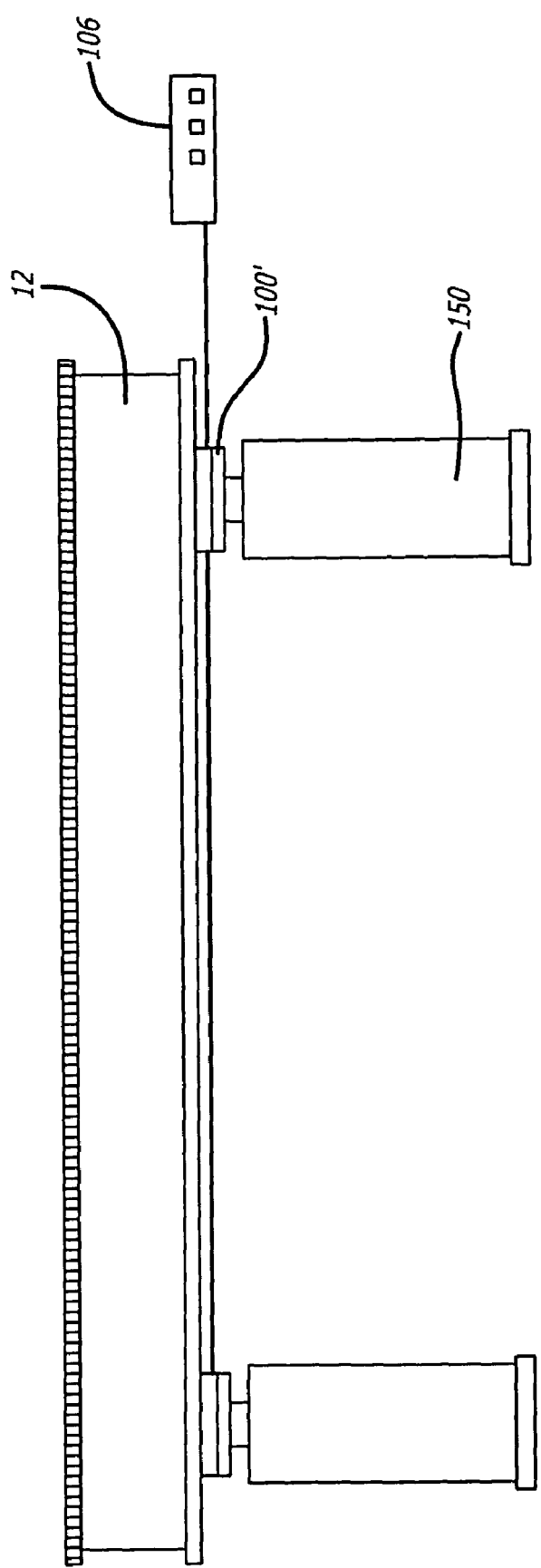
FIG. 9 is a side view of an optical table assembly with a vibration damper assembly located between a table of the optical table assembly and a vibration isolator of the optical table assembly.

FIG. 9 shows an embodiment of a table assembly with a vibration damper assembly 100' located between an optical table 12 and a vibration isolator 150. The function of the vibration isolator 150 is primarily to isolate the table 12 from vibration of the floor. The vibration damper assembly 100' and isolator 150 are in separate housings which allows an operator to add, or remove the damper assembly 100' from the table assembly. The vibration isolator 150 may be of any suitable type known in the art. The separate damper assembly 100' provides an operator of the table assembly with flexibility in damping vibration in the table 12. Although not shown in FIGS. 1, 3 and 7, it is to be understood that the table 12 of those figures shown may be supported by the isolator 150 or any other structure such as table legs.

Figure 10:
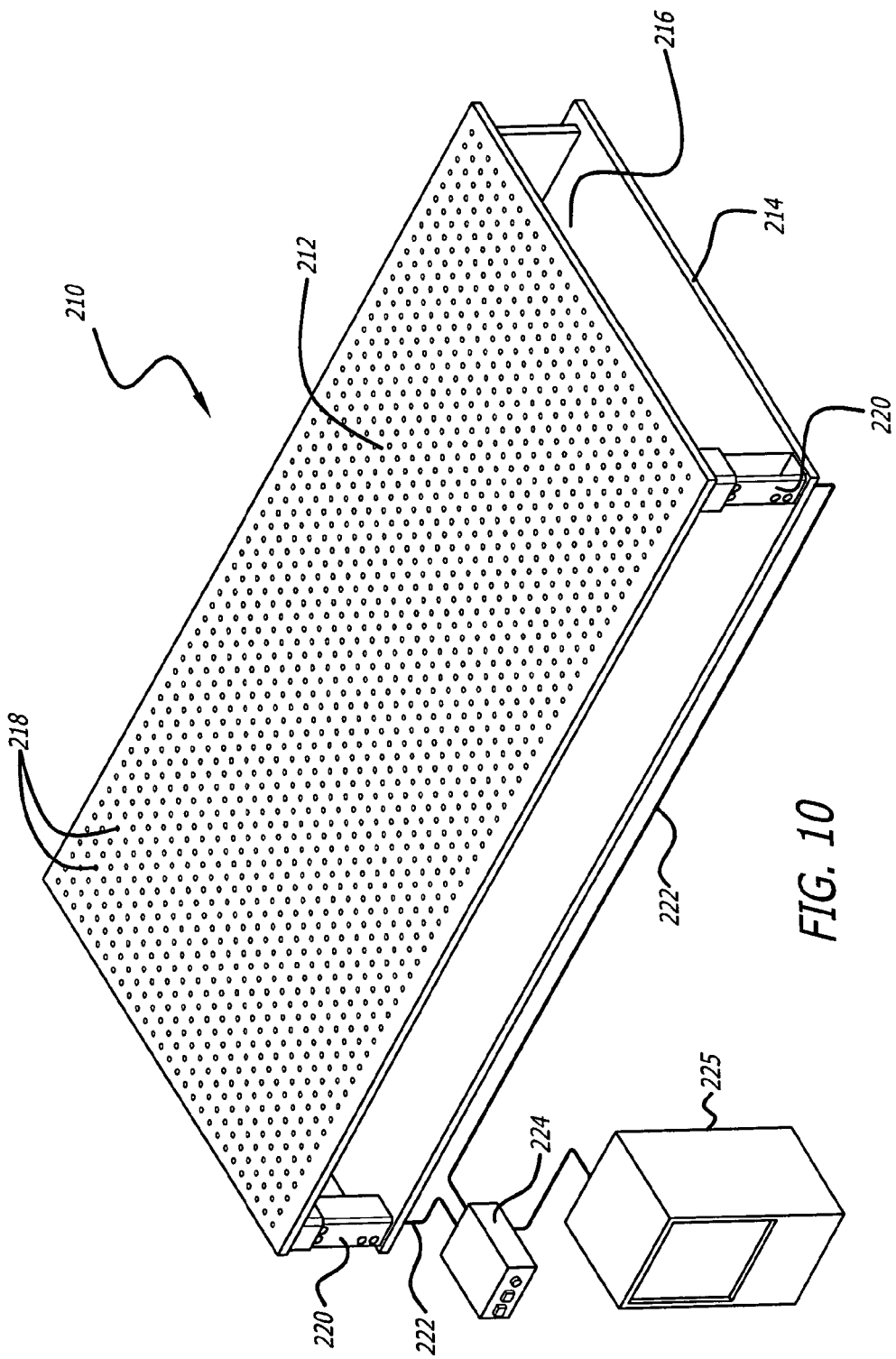
FIG. 10 is a perspective view of an optical table or platform that includes two vibration damper assembly embodiments coupled to a controller.

FIG. 10 shows an embodiment of an optical structure in the form of an optical support structure or platform having two active vibration damper devices or assemblies 220 integral therewith or otherwise coupled thereto. In the illustrated embodiment, the optical support structure 210 includes a first surface 212, a second surface 214, and a core 216 therebetween. In one embodiment, at least one of the first surface 212 and the second surface 214 may be configured to have one or more optical elements and/components, mounts, and/or measuring devices coupled thereto. For example, in the illustrated embodiment, the first surface 212 of the optical support structure 210 includes one or more apertures 218 configured to receive and engage at least a portion of an optical component in the form of an optical mount (not shown). Optionally, the second surface 214 and/or the structure body 216 of the optical support structure 210 may likewise include one or more apertures 218 formed thereon. In one embodiment, the one or more apertures 218 may be sealingly formed within the optical support structure 210 having cups disposed about the one or more apertures 218 to prevent leakage of materials or parts into the structure body 216. Further, embodiments of the one or more apertures 218 may be threaded and capable of receiving at least one optical component such as an optical mount in threaded relation therein. Finally, for some embodiments, the one or more apertures 218 may be numerous and evenly spaced at regular intervals, such as an orthogonal grid of apertures 218 spaced about 0.5 inch to about 1.5 inches apart.

Referring again to FIG. 10, the first surface 212, the second surface 214, and the structure body 216 may be constructed of any variety of materials. For example, at least one of the first surface 212, the second surface 214, and the structure body 216 may be constructed of one or more materials including, without limitation, stainless steel, titanium, iron, cast iron, aluminum, carbon fiber, granite, steel, carbon steel, laminated metals, composite metals, wood, laminated woods, composite woods including medium density fiber board, particle board, cardboard, multiple component laminates, formica, formica covered substrates, fiberglass, composite materials, Kevlar®, and the like. In one embodiment, the first and second surfaces 212, 214, respectively, may be constructed from stainless steel while the structure body 216 is constructed from aluminum. Optionally, in one embodiment, the structure body 216 may be constructed of a honeycomb structure and configured to provide support for the first and second surfaces 212 and 214. Optionally, the structure body 216 may be constructed without a honeycomb structure.

As shown in FIG. 10, the vibration damper assemblies 220 may be coupled to or otherwise in communication with at least a portion of the optical support structure 210. In the embodiment shown in FIG. 10, both the damper assemblies 220 are integrally secured to the optical support structure 210. In some embodiments, however, one or more of the damper assemblies 220 may be detachably coupled to any portion of the support structure 110, including at least one of the first surface 212, the second surface 214, and/or the structure body 216. Any variety or number of damper assemblies 220 may be secured, coupled or in communication with the optical support structure 210, including 1, 2, 3, 4, 5, 6 or more active vibration damper assemblies 220. The discussion above with regard to FIGS. 1-9 discloses a number of vibration damper devices or assemblies 50, 80 and 100, any combination of which may be used in conjunction with active damper assembly 220 with the optical support structure 210.

The damper assemblies 220 may be secured to the support structure 210, or any portion or component thereof, such as at least one of the first surface 212, the second surface 214, and/or the structure body 216. In the illustrated embodiment, the active damper assemblies 220 are positioned proximate to the structure body 216 and are in communication with the first surface 212 and the second surface 214. In addition, the damper assemblies 220 are disposed at corners of the optical support structure 210 which has a generally rectangular configuration for the embodiment shown. The damper assemblies 220 may, however, be disposed at any desired position on the optical support structure 210.

The damper assemblies 220 may be secured to the optical support structure 210 in any variety of ways, including, without limitation, magnetically secured, mechanically secured, screwed, bolted, or otherwise secured thereto with one or more threaded members. The damper assemblies 220 may also be secured to the optical support structure with one or more tracks or attachment devices positioned on the optical support structure 210, using vacuum force, using gravitation force, adhesively secured or bonded, or the like. Exemplary fastening devices for securing the damper assemblies 220 to the optical support structure 210 include, without limitation, screws, bolts, threaded members, rivets, lock pins, nails, tacks, locking members, and the like.

Figure 11:
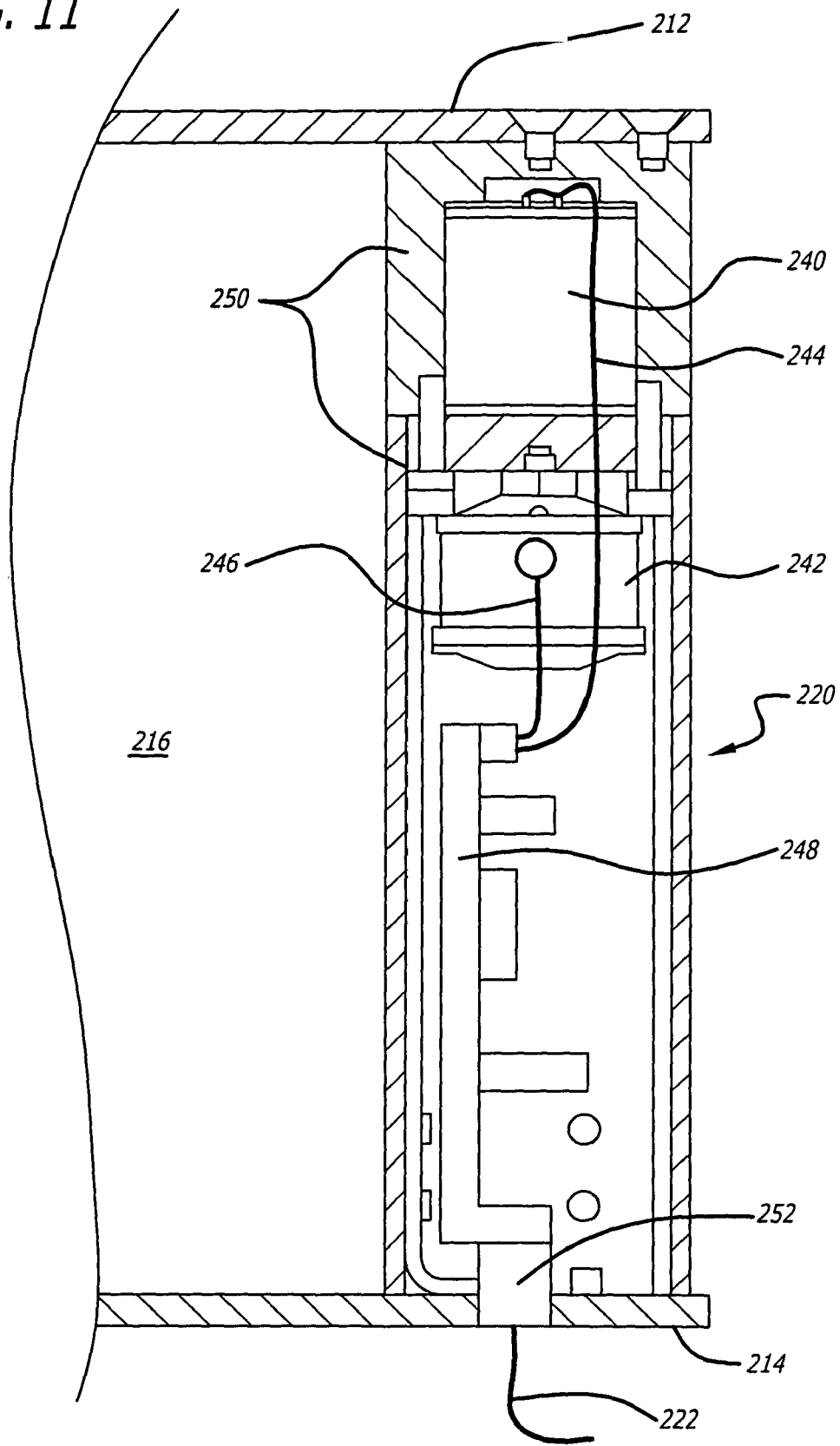
FIG. 11 is an elevation view in partial section of a vibration damper assembly embodiment that is configured to actively damp vibration and includes a vibration sensor, an actuator, a driver device and a housing.

Referring to FIG. 11, the active vibration damper device or assembly 220 may include one or more sensors 240 and one or more vibration actuators 242. The vibration actuators 242 may also include one or more active elements, flexural or spring members and mass members as discussed above. The sensor 240 may include vibration sensors, accelerometers, geophones, or other sensors. Exemplary actuators for the actuator 242 may include, without limitation, electrodynamic devices, electromagnetic devices, piezoelectric devices, and any other suitable actuator. One particular active element of the actuator 242 may include a voice coil device or the like.

For some embodiments, the sensor 240 and actuator 242 are disposed in a co-axial orientation. In other embodiments, the sensor 240 and actuator 242 are not co-axially oriented. Similarly, the sensor 240 and actuator 242 may or may not be oriented in a direction perpendicular to at least one of the first surface 212, the second surface 214, and/or the structure body 216. The sensor 240 may be coupled to an optional driver device 248 disposed adjacent the actuator 242 with at least one conduit 244 that is configured to carry information or energy such as an electrical wire or wires. Similarly, the actuator 242 may be coupled to the driver device 248 with a similar or other suitable conduit 246. Optionally, the sensor 240 and actuator 242 may be wirelessly coupled to the driver device 248. The driver device 248 may include a pre-amplifier and be configured to receive a signal or signals from the sensor 240, amplify the signal and communicate the amplified signal to a controller. The driver may also include amplifiers configured to amplify control signals from the controller and transmit the amplified signal or signals generated therefrom to the actuator 242.

As shown in FIG. 11, the various elements of the vibration damper assembly 220 may be positioned within a single housing or casing 250. Optionally, the damper assembly 220 may comprise a number of housings configured to be interconnected, thereby providing a modular damper device design capable of being configured for specific applications of users depending on their needs. For example, a damper assembly 220 may have a variety of sensors. In another embodiment, a damper assembly 220 having a variety of actuators 242 may be used. As shown in FIG. 11, at least one connector 252 is in communication with the driver device 248 thereby permitting the conduit 222 coupled to the controller 224 (See FIG. 10) to be coupled to the driver device 248.

Referring again to FIG. 10, the damper assembly 220 is in communication with at least one controller 224 configured to receive information from the damper assembly 220 and provide information or control signals to the damper assembly 220. For some embodiments, the controller 224 is coupled to the damper assembly 220 through one or more conduits 222. Optionally, the controller 224 may be in communication with the damper assembly 220 using a wireless communication system, free space communication systems, laser communication system, or the like. In the illustrated embodiment, the controller 224 comprises a stand-alone device coupled to the damper assembly 220 with the conduits 222. Optionally, the controller 224 may be coupled to the optical support structure 210 or integrally secured within a portion of the optical support structure. During use, an embodiment of the controller 224 receives vibrational information from at least one of the damper assemblies 220 and provides one or more signals to one or more damper assemblies 220 in communication with the optical support structure 210 in a control loop configuration, thereby providing an active damping architecture. Such vibrational information and signals may optionally be communicated through the driver device 248 which may be disposed within the housing 250 or disposed in some other suitable location, including near or within the controller 224 itself.

Any suitable type of device or processor may be used as a controller 224, including, without limitation, computers, micro-processors, integrated circuits devices, measuring devices, and the like. Optionally, the controller 224 may be in communication with one or more sensors 240 located within the damper assemblies 220 or coupled to the optical support structure 210 at any location. In addition, controller 224 may be coupled to a display 225 that may be used to display the status of the controller 224, vibration information from the sensors 240, as well as allow interactive programming of the controller 224 to achieve a desired vibration damping result. The display 225 may be used in conjunction with a computer or other processor (not shown) that may be used to facilitate the display of information or interactive programming of the controller 224.

Figure 12:
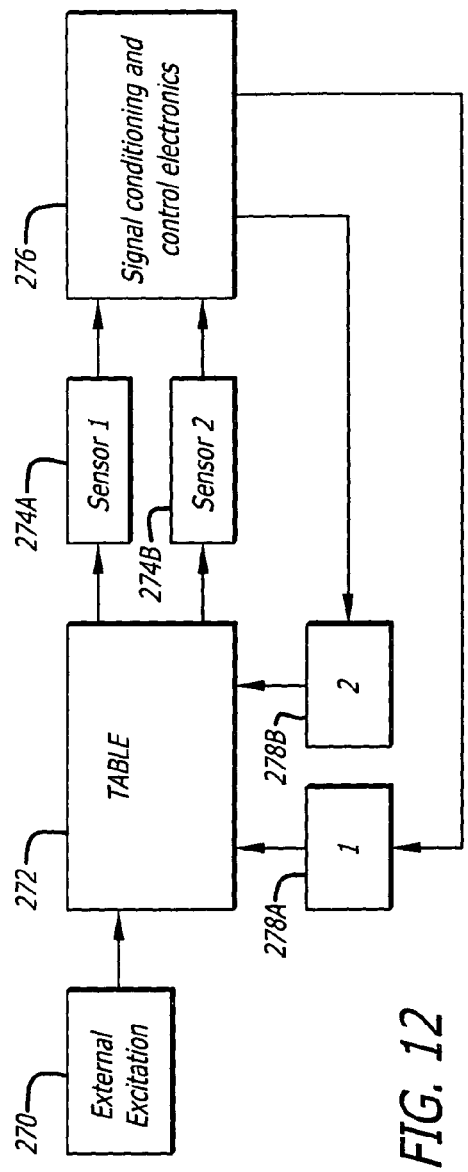
FIG. 12 is a block diagram illustrating a method of active damping of an optical table or other low vibration surface or structure.
Figure 13:
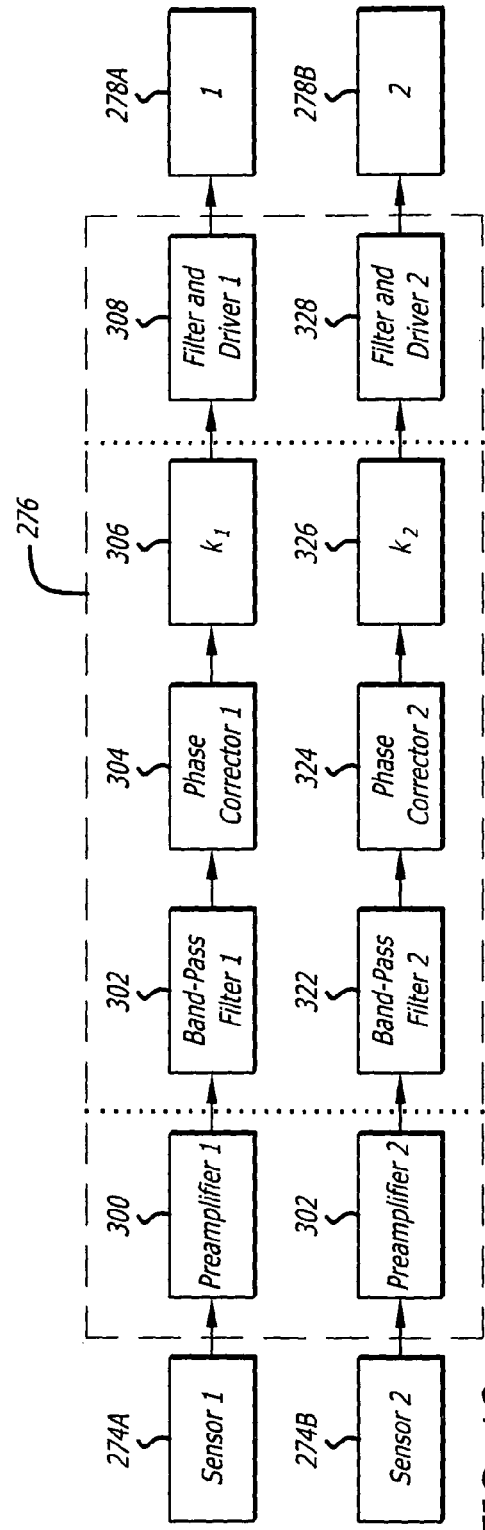
FIG. 13 is a block diagram illustrating a dual control channel method of active vibration damping.

FIGS. 12 and 13 show block diagrams illustrating method embodiments of damping vibration in an optical structure such as optical support structure 210. As shown in FIG. 12, an external excitation 270 is incident upon an optical support structure 272, which may be the same as or similar to optical support structure 210, and received by at least one sensor 274 located therein or in communication therewith. In the illustrated embodiment, a first sensor 274A of a first actuator device (See FIG. 10) and a second sensor 274B of a second actuator device may be used. The first sensor 274A and second sensor 274B may be integral with the optical support structure 272. Also, the first sensor 274A and second sensor 274B may be positioned on the first surface 212. Note that the sensors 274 may be the same as or similar to the sensor 240 discussed above. The first and second sensors 274A, 274B, respectively, generate and send a signal to a controller in the form of the signal conditioning and control electronics section 276, which is shown in more detail in FIG. 13.

In some embodiments, the signal conditioning and control electronics section 276 may include the driver device 248 (See FIG. 11) and/or the controller 224 (See FIG. 10), which processes the vibration signal information. As such, at least one driver device 248 (See FIG. 11) and/or the controller 224 (See FIG. 10) includes one or more algorithms configured to generate a control signal to be transmitted to at least one active element 278A or 278B of corresponding actuators, which may be the same as or similar to the actuators 242 above, in communication with the optical support structure 272. In some embodiments, the control signal may be tuned to drive the active elements 278A and 278B with an optimal vibration-canceling output. As such, embodiments of the system disclosed herein enable a user to monitor the vibrational characteristic of a structure within an environment and provide an actively damped architecture. For example, in some embodiments, the vibration damper assembly and controller system provides auto-ranging architecture which utilizes a mean-square value of a feedback signal.

FIG. 12 shows an embodiment of a feedback or control loop schematic for the control of damping systems used for reducing vibration of an optical structure. Although two sensors 274A and 274B and two active elements 278A and 278B are shown, any number of sensors 274A, 274B and active elements 278A, 278B may be used. The vibration damper system may be operated in multiple-input-multiple-output (MIMO) format, where the signal to each actuator 242 is derived from all the vibration sensors 240. However, for some embodiments, it is useful for stability and robustness to operate the vibration damper system as a conglomeration of several independent vibration damper devices or assemblies 220 each having a respective sensor 240 and adjacent actuator 242. Each damper assembly 220 in such a system may be operated by a separate control channel of the controller 224. Embodiments of these control channels are shown in more detail in FIG. 13. The control functions include gain factors K1 and K2 that define trade offs between damping performance and system stability. It may be useful, in some embodiments, to take the gain factors as high as possible for increasing damping power and thereby decreasing unwanted vibration of the optical support platform 210 at a higher rate. However, in some cases, if the feedback gain factors are too high, the system may become unstable. To determine fixed optimal gain factors that include an acceptable stability safety margin would normally require detailed knowledge of the complete mechanical model of the plant or system including all resonant vibrational modes of all components in combination. Even if such information were available or readily discernable, the optimal gain factors may change over time because of variations in temperature, payload on the support structure 210 etc. As such, methods and devices for adaptively tuning the vibration damping system are discussed below with regard to FIG. 14.

Referring to FIG. 13, an embodiment of a control channel pair for use with an actively damped optical structure, such as optical support structure 210, is shown. As shown, a first pre-amplifier 300 of the signal conditioning and control electronics section 276 receives an input signal from the first sensor 274A. The first pre-amplifier 300 processes the input signal and transmits a processed signal to a first band-pass filter 302. Thereafter, the filtered signal is transmitted by the first band-pass filter 302 to a first phase corrector 304. Thereafter, a first gain factor $K_1$ is applied to the phase corrected signal. Thereafter, a gain factored signal is sent to a first filter and driver 308 which processes the signal and drives the first active element 278A. In some embodiments, the first pre-amplifier 300, the filter and driver 308 or both may be included in the driver unit 248 discussed above. Similarly, the second pre-amplifier 302 of the signal conditioning and control electronics section 276 receives an input signal from the second sensor 274B. The second pre-amplifier 302 processes the input signal and transmits a processed signal to a second band-pass filter 322. Thereafter, the filtered signal is transmitted by the second band-pass filter 322 to a second phase corrector 324, the phase correction step of which may be implemented by software processes. Thereafter, a second gain factor $K_1$ is applied to the phase corrected signal as shown in box 326. The application of the second gain factor $K_1$ may also be implemented by software processes. Thereafter, a gain factored signal is sent to a second filter and driver 328 which processes the signal and drives the second active element 278B. In some embodiments, the first pre-amplifier 302, the filter and driver 328 or both may be included in the driver unit 248 discussed above. In some embodiments, any variety or combination of similar control architectures could be used with the vibration damper assemblies 220 and controllers 224.

These methods of producing a vibration suppression or damping signal to the actuators 242 may also be adapted to work in a wide range of practical applications and diverse working environments. The practical levels of environmental vibration encountered by optical support structures or platforms 210 can vary significantly, and variations of three orders of magnitude in vibration amplitude are not uncommon. For some environments, vibration variations may range from sub-micron per second RMS amplitudes in quiet laboratories to significant fractions of a millimeter per second RMS in commercial production facilities, such as semiconductor wafer production facilities. In order for the controller 224 to maintain its vibration damping performance in conjunction with the damper assembly 220 under these varied conditions, it must monitor the vibration feedback signal from the vibration sensor 240 and maintain the signal-to-noise ratio, phase, bandwidth as well as other characteristics of that signal as well as the same or similar properties of the control signal to the vibration damper assembly 220. Embodiments of the controller 224 are configured to use a auto-ranging method that utilizes the mean-square value of the vibration feedback signal from the sensor 240 in order to monitor the output amplitude of the vibration signal and adjust gain parameters as well as other factors in order to maintain proper signal-to-noise ratio, phase, bandwidth as well as other characteristics. Other features of the vibration feedback signal from the sensor 240 may also be monitored, such as maxima and minima of the signal.

For some embodiments, a method of automatically selecting an appropriate range of input vibration signal detection in an active damper assembly, includes providing a vibration damper system having an active damper assembly 220 with a vibration sensor 240 and an actuator 242 and including a controller 224 coupled to both the sensor 240 and the actuator 242 by a control channel, such as the control channels shown in FIG. 13. The controller 224 may also have at least two vibration feedback signal inputs with gain factors appropriate to the signal strength range for the vibration signal amplitude. The vibration feedback signal from the sensor 240 is monitored by the controller 224, and specifically, for some embodiments, the mean-square value of the vibration signal from the sensor 240 is monitored. The mean-square value of the vibration feedback signal is then compared to a pre-selected range of signal values over a pre-selected period of time by the controller 224. If the monitored signal violates some desired constraints, such as being outside the pre-selected range of signal values, for a period of time, then a different and appropriate feedback signal range input is selected or switched to by the controller which has a gain factor appropriate for the mean-square value of the vibration input signal amplitude into the controller 224.

For example, if the vibration feedback signal, or mean-square value thereof, has a value over a period of time that exceeds the pre-selected range of the selected feedback signal input of the controller 224, the controller 224 will switch the vibration feedback signal to a different input that may have a lower gain factor, so as not to over amplify the vibration feedback signal and avoid excessive noise or have to low a signal-to-noise ratio. In the alternative, if the vibration feedback signal, or mean-square value thereof, has a value over a period of time that is below the pre-selected range of the selected feedback signal input of the controller 224, the controller 224 will switch the vibration feedback signal to a different input that may have a higher gain factor, so as not to under amplify the vibration feedback signal. In some cases, the pre-selected range in the lowest range gain factor of signal inputs of the controller 224 may still be violated, in which case a vibration overload condition may be said to exist. In such a situation, the controller 224 may present an error signal, such as a visual or audio signal, to the user of the system. In addition, the controller 224 may be configured to shut down the vibration damping process in these circumstances. The overload condition may also be detected with an error signal generated by a signal clipping detector or detectors in the preamplifier.

Similar overload conditions may also be used to detect changes in payload on the surface of the optical support platform 210 and making adjustments, such as adjustments in the gain factors of the control loops in response to the change in order to adapt thereto. Performance of embodiments of the vibration damper system may need to be insensitive to changes in payload properties or amounts on the surface or other locations of the optical support platform 210. The equipment positioned on the platform 210 may vary from lightweight to weights comparable to the weight of the optical support platform 210 itself, or even greater. If the control loop gains K1 and K2 were tuned for a particular payload configuration and if the payload is changed, there is potential for the controller 224 to become unstable. In such circumstances, the controller 224 may be configured to identify the onset of instability and execute some instructions to remedy the situation or alert the user of the situation. For example, the controller 224 may be configured to shut down the control system or re-tune the control loop either with, or without user intervention.

An embodiment of a method of automatically adjusting gain factors in an active damper system for changes in payload, may include providing a vibration damper system including a vibration damper assembly or device 220 with a vibration sensor 240 and an actuator 242 and including a controller 224 coupled to both the sensor 240 and the actuator 242 by a control channel, such as the control channels in FIG. 13. The controller 224 may have a vibration feedback signal input with gain factors appropriate to the signal strength range for the vibration signal input. The vibration feedback signal from the vibration sensor 240 is monitored for vibration overload conditions. A vibration overload condition may exist, as discussed above, when the pre-selected range in the lowest range gain factor of signal inputs of the controller 224 are still violated. If a vibration overload condition exists, the controller 224, or rather the drive signal of the controller 224 to the actuator 242, is disabled and a subsequent determination is made as to whether the vibration overload condition still exists. If the vibration overload condition ceases when the drive signal to the actuator 242 by the controller 224 is disabled, a change in payload on the optical support platform 210 has taken place. It may now be appropriate to recalibrate the gain factors in order to accommodate the change in payload.

Figure 14:
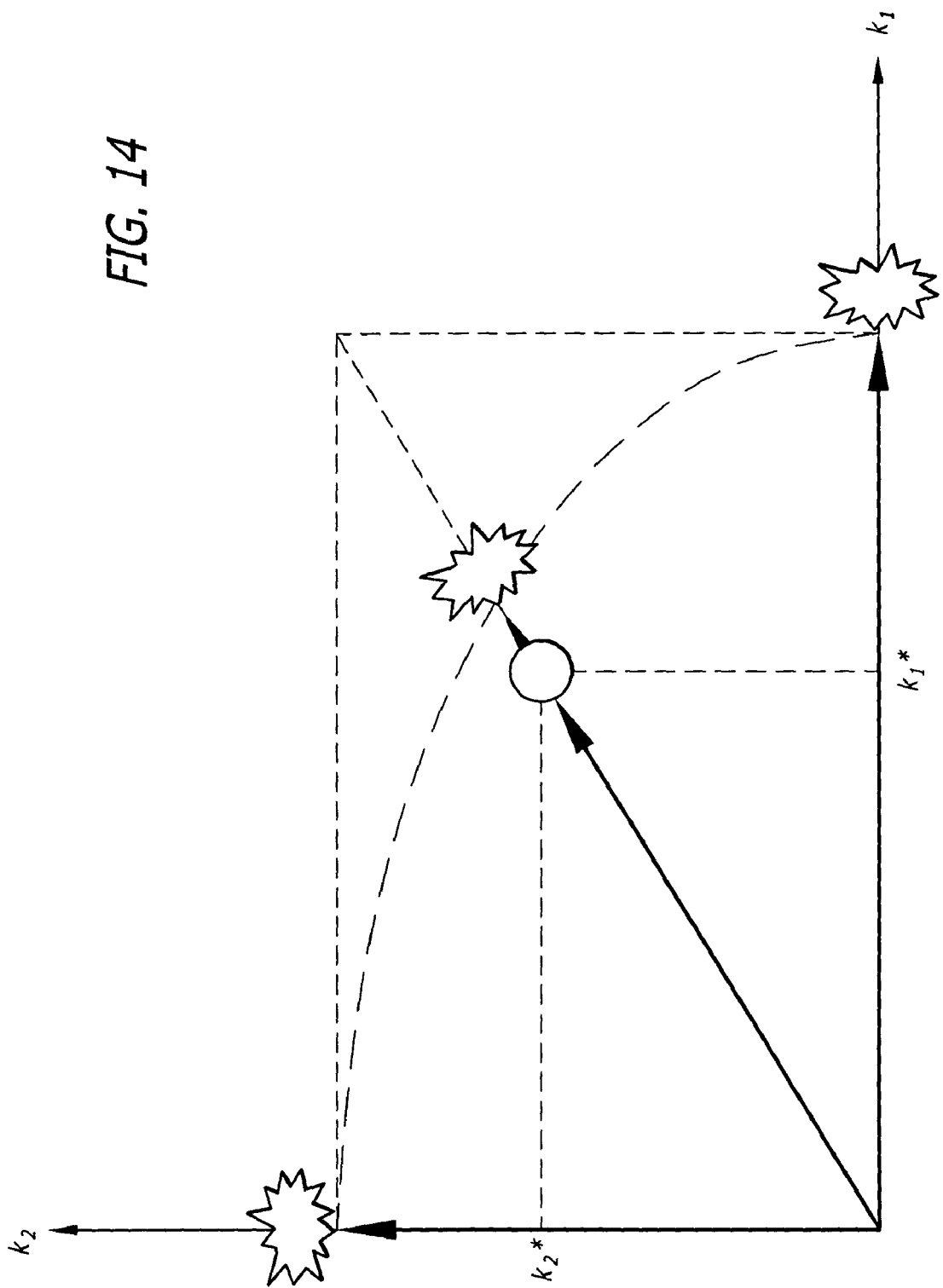
FIG. 14 is a graphical representation of a method of determining gain factors for a controller of an active vibration damper system utilizing adaptive tuning.

FIG. 14 shows a graphical representation of a damping process which is specifically configured to determine a gain factor or factors that will provide good performance and vibration damping. In some embodiments, a method of adaptively tuning the gain factors of the control channels of the controller 224 includes providing a vibration damper system including one or more vibration damper devices with a vibration sensor 274 and an active element 278 of an actuator 242 and including a controller 224 coupled to both the sensor 274 and the active element 278 by a control channel, such as the control channels shown in FIG. 13. Initially, all control channels except one active channel are disabled or shut down. In the remaining active control channel, the gain factor is increased until instability of the system is detected by the vibration sensor 274. The gain factor is then reduced by a small increment or increments in order to re-achieve system stability. The highest gain factor that achieved stability is then stored into a memory unit, such as a non-volatile memory device.

An example of a non-volatile memory device may include an EEPROM memory chip. The procedure is then repeated for the remaining control channels with all control channels being shut down except for the remaining active control channel for which the gain factor will be optimized and stored. All control channels are then activated and the gain factors to each control channel increased in an amount proportional or substantially proportional to the stored gain values for each respective channel. The gain factors of each control channel are proportionally increased until instability of the vibration damper system is again detected by the controller 224 by monitoring the vibration feedback signal or signals from the vibration sensor or sensors 274. The gain factors are then reduced in small steps for all control channels until stability is achieved for the vibration damper system. For some embodiments, gain factors for each control channel are reduced in small steps proportional to the stored gain factor simultaneously to regain stability if necessary. While the controller 224 is reducing the gain factor of a control channel in order to re-achieve stability of the system, a variety of approaches may be used to expedite the determination of the acceptable gain factor. For example, in one embodiment, the determination of the maximum gain factor that will produce a stable system or system component is carried out by a converging search method. In some cases the converging search includes a bisection method. In addition, it may be desirable after a gain factor has been reduced to achieve stability, to further apply a safety factor reduction to each of the gain factor values. The safety factor reduction may be about 5 percent to about 50 percent of the base gain factor. In other embodiments, other monotonous functions of gain values may be used instead of direct proportionality to increase or reduce the gain values in each control channel, such as power laws, exponential laws or logarithmic laws.

Figure 15A:
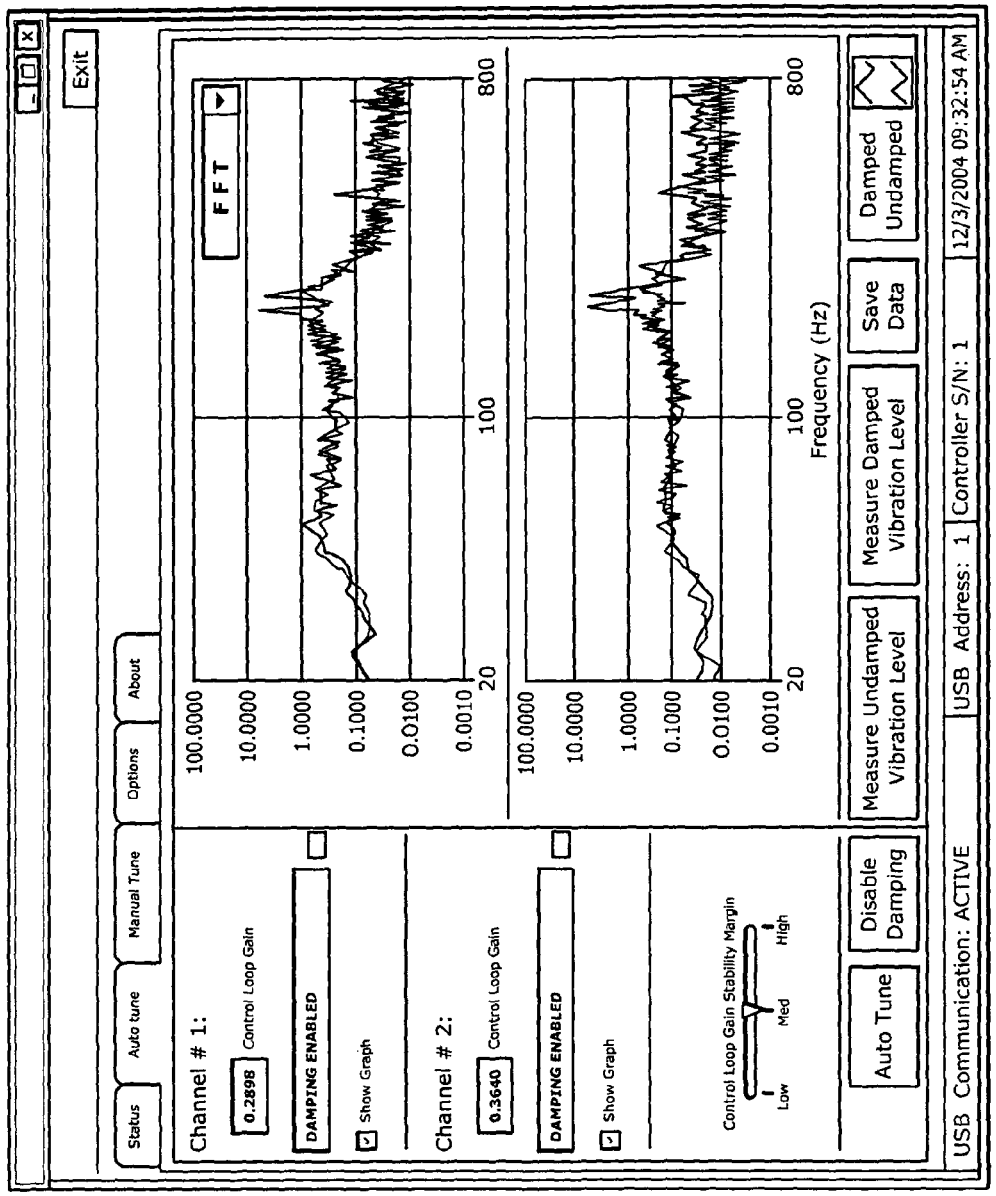
FIGS. 15A-15C illustrate representations of interactive screen displays on a display of an embodiment of a controller.
Figure 15B:
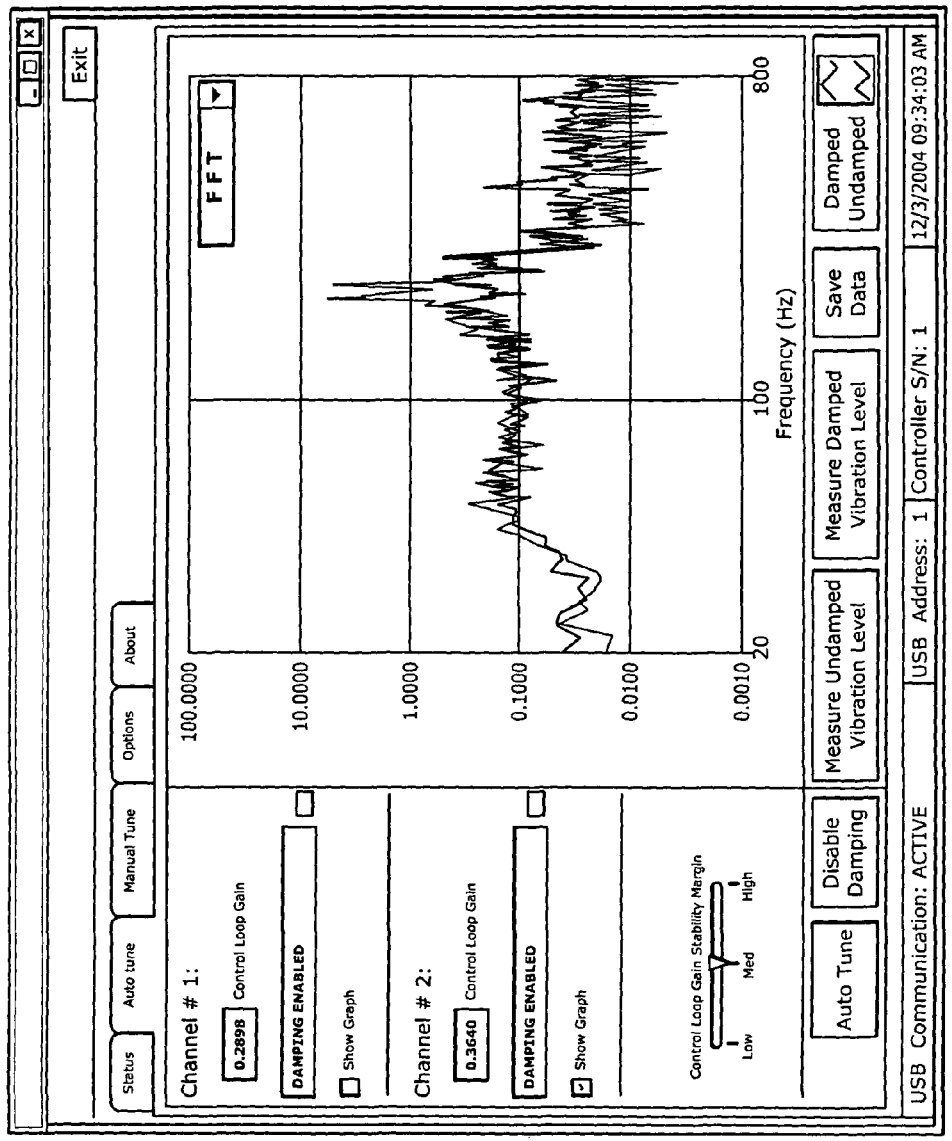
Figure 15C:
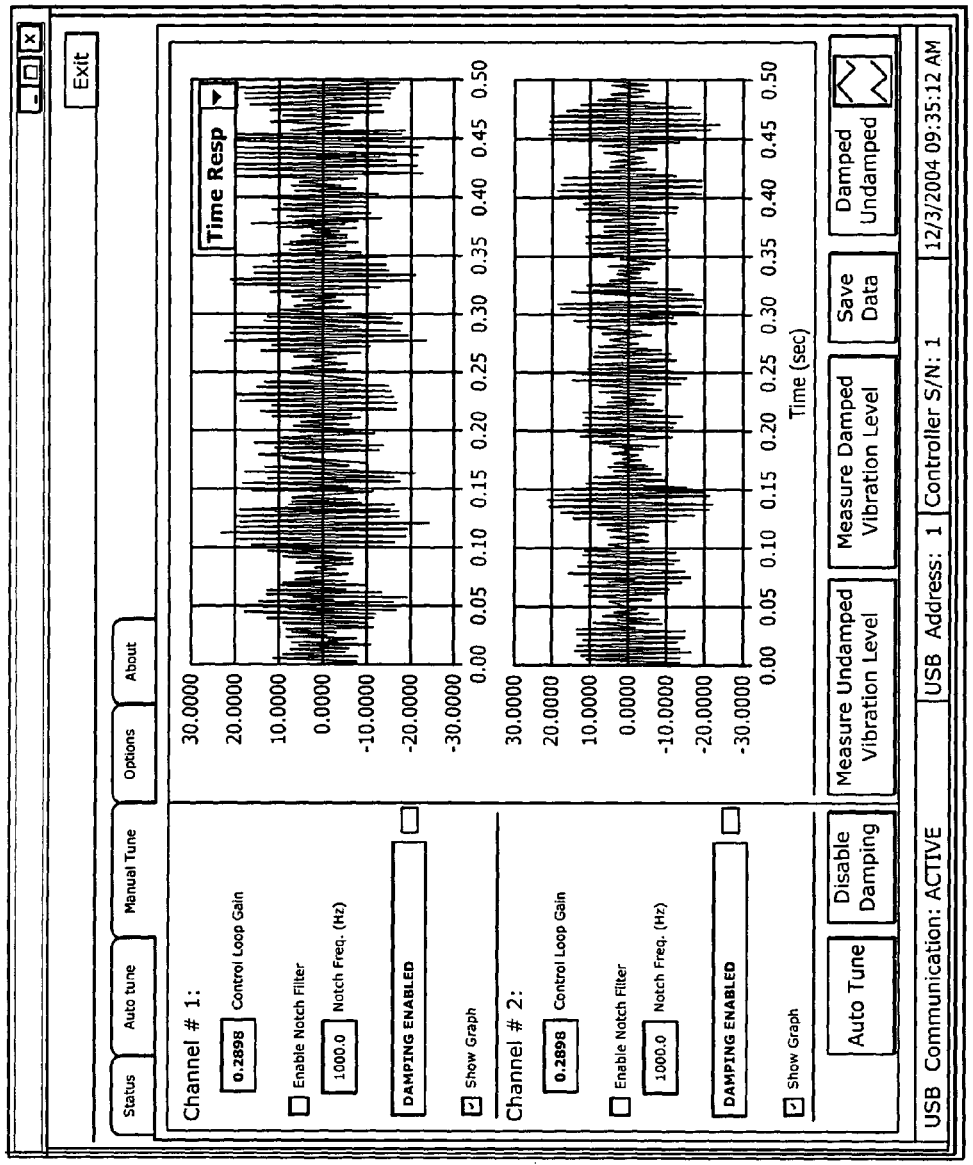

FIGS. 15A-15C illustrate various screen displays on the display 225 of the controller 224 which is coupled to two vibration damper assemblies 220. A similar display may be used for any number of controllers 224 or vibration damper assemblies 220, or components thereof. FIG. 15A shows a screen shot of the display 225 while the controller is in an "auto tune" tab. The display shows the status of some of the controller settings and a dual channel graphical display of vibration amplitude as measured by the two vibration sensors 274A, 274B versus frequency of the vibration; the graphs obtained with damping disabled and enabled are superimposed for comparison. FIG. 15B shows the "auto tune" tab with a single channel display of vibration amplitude versus vibration frequency of vibration signals obtained with damping disabled and enabled superimposed on each other for comparison. FIG. 15C shows a screen shot of the display 225 of the controller with the controller disposed in "manual tune" mode or tab. This tab provides direct control over the gain factors of the respective control loops of the damper assemblies 220. Both of the display tabs display the gain factor for each control loop, the frequency of a notch filter which may optionally be enabled. The status of active damping, whether enabled or disabled is shown along with a menu to make the selection between the two. The graphical display in the right hand portion of the display may be configured to show an undamped vibration signal and a damped vibration signal. It may also be configured to show a signal in either frequency domain or time domain.

Referring again to FIG. 15A, the various interactive display "buttons" may be selected to display or activate certain features. For example, clicking on "Enable Damping" or "Disable Damping" buttons will enable or disable active damping by the system. If damping is enabled, the "Disable Damping" button is visible, and vice versa. By clicking on the "Measure Undamped Vibration Level" button, the vibration level will be recorded and displayed with the active damping by the active elements 278 of actuators 242 disabled. The vibration data may be averaged over several time frames and the number of time frames for averaging may be selected by the user in the "Options" tab. By clicking on the "Measure Damped Vibration Level" button, the damped vibration level will be recorded and displayed. The data may be averaged over a similar time period to that of the undamped vibration level and may also be averaged over several time frames. Both the damped and undamped vibration levels may be displayed in either frequency domain or time domain by selecting either "FFT" or "Time Response" from the pull down menu on the display. The FFT display resolution may be about 0.5 Hz to about 5 Hz. The selection between single channel or dual channel display of vibration levels may be made by selecting the "Show Graph" button. The "Save Data" button may be activated to save the displayed data. If the "HTML" option is selected in the "Options" tab, all graphs are saved in HTML file format. If the "Text" file option is selected in the "Options" tab, the measured data will be saved in two text files. The first file is used to store time response data and the second file is used to store frequency response data.

Figure 16:
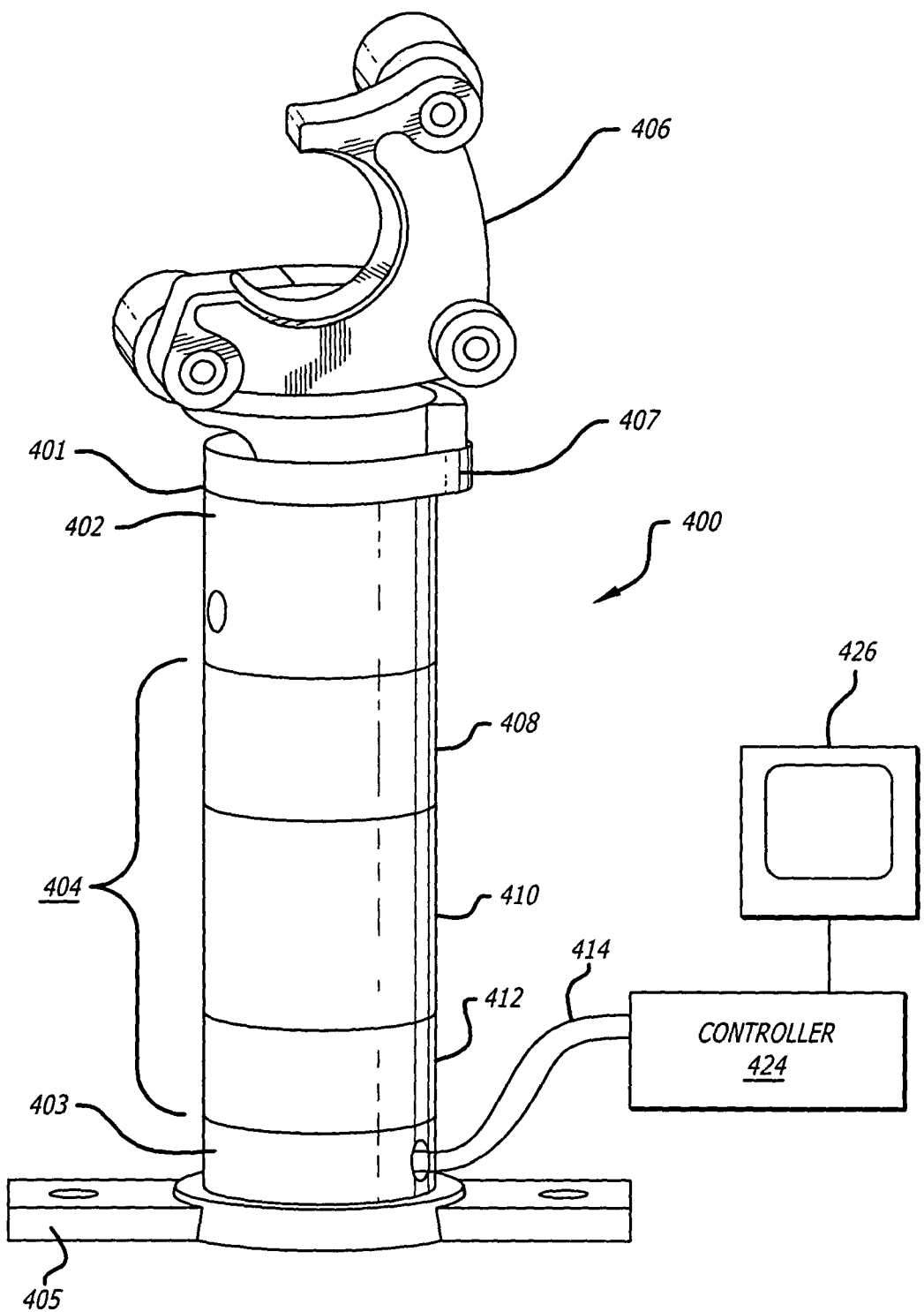
FIG. 16 is a perspective view of an optical structure which is an optical component in the form of an optical post having a lens mount device at a top of the post and a vibration damper assembly disposed within a body portion of the post which is coupled to a controller.
Figure 17:
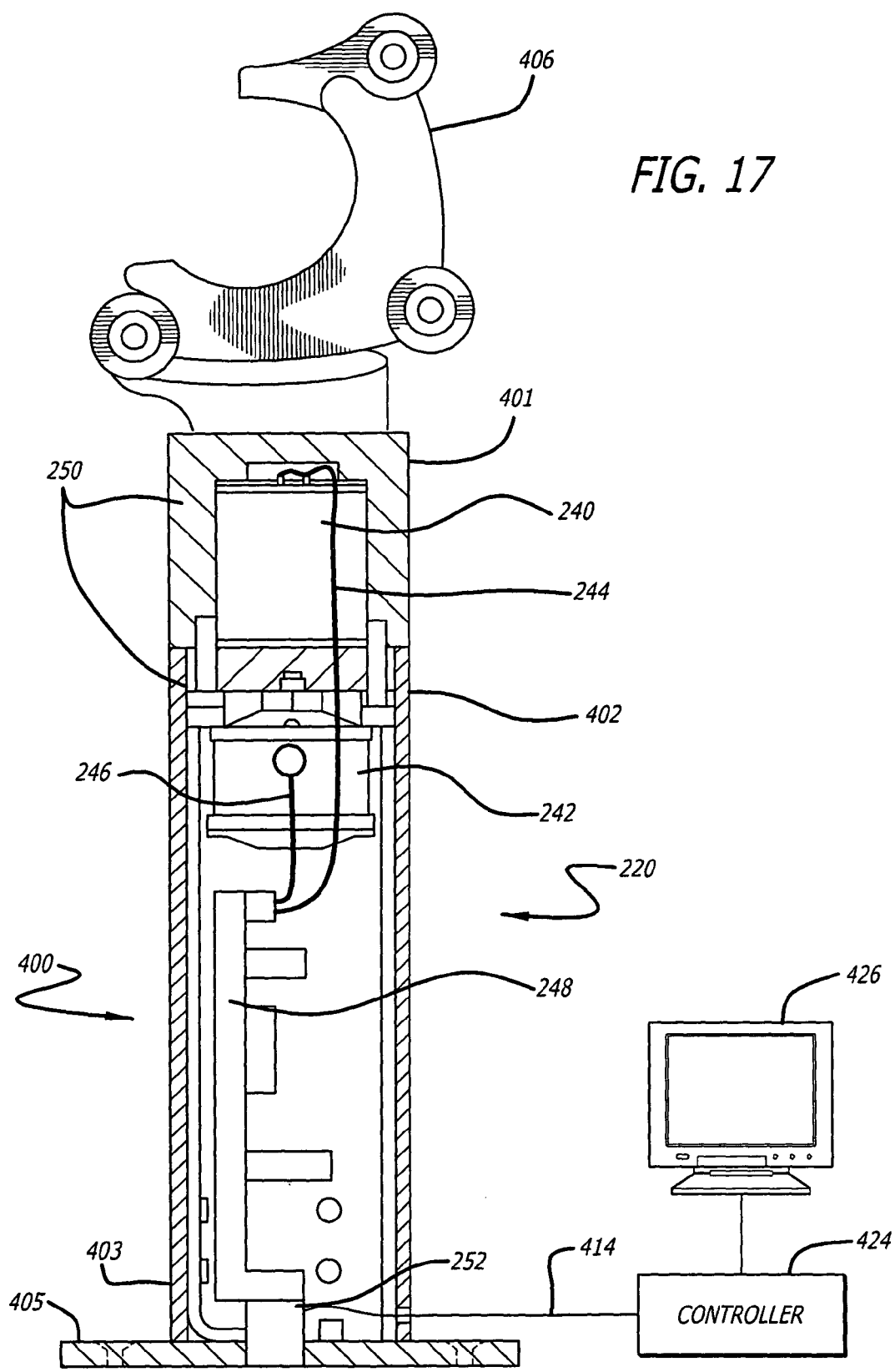
FIG. 17 is an elevational view in partial section of optical component of FIG. 16.

FIGS. 16 and 17 show an alternate embodiment of an optical structure in the form of an optical component 400 that includes a vibration damper assembly 220 such as the vibration damper 220 shown in FIG. 11. As shown, the optical component 400 in the form of a vertical post mount includes a body portion 402 having a vibration damping device or assembly 220 coupled thereto or disposed therein within a damper section 404 of the body portion 402. The body portion 402 has an upper end 401 and a lower end 403. In some embodiments, the body portion 402 may have a mount plate 405 secured to the lower end 403 of the body portion 402. The mount plate 405 may be configured to be secured or coupled to another optical support structure or platform, such as an optical table, bench, fixture, or the like using any number of attachment methods, including, without limitation, mechanical attachment, magnetic attachment, adhesive attachment, welded attachment, detachably attachment techniques, and non-detachable attachment methodologies. An optical mount device in the form of a lens holder 406 is secured to a mount plate 407 disposed on the upper end 401 of the body portion 402.

Embodiments of the mount plate 407 may be detachably secured to the upper end 401 of the body portion 402 or, in other embodiments, permanently secured thereto. The mount plate 407 has a mount surface or structure (not shown) that may allow standard optical mount components, such as lens holders, laser mounts, and the like, to be detachably secured to the mount plate 407. In this way, optical mount components may be mounted directly to an optical support structure that has an active vibration damper device or assembly integrally mounted thereon or coupled thereto. Such an active vibration damper assembly may be tuned specifically to the resonant frequencies and frequency ranges of the optical component 400, which may differ from the resonant vibrational frequencies and frequency ranges of the underlying table or platform, such as the optical substrate 210, as shown in FIG. 10, to which the optical component 400 may be mounted.

The body section 402 may include one or more vibration sensors 240 disposed therein and one or more active vibration actuators 242 having one or more active elements therein. A driver 248 may be coupled to the vibration sensor 240 and actuator 242. In essence, one or more embodiments of the vibration damper assemblies 220 (not shown), discussed above, may be integrated into the body portion 402 of the optical component 400. As such, the vibration damper assembly is indirectly mechanically coupled to the optical mount device or lens holder 406 and may be used to suppress or cancel mechanical vibration of the optical mount device 406.

At least one controller 424 may be coupled to the vibration damper assembly 220 disposed within the body section 402 by conduits 414. Optionally, the controller 424 may be in wireless communication with the vibration damper assembly 220 disposed within the damper section 404. In alternate embodiments, at least one controller 424 may be positioned within the body portion 402. Embodiments of the controller 424 may operate in a manner the same as, or similar to, the manner of operation of the controllers 224, 106 and 64 discussed above. In addition, controller 424 may be coupled to a display 426 that may be used to display the status of the controller, vibration information from the sensor 240, as well as allow interactive programming of the controller 424 to achieve a desired vibration dampening result.

In the illustrated embodiment, the mount device 406 includes an optic mount device in the form of a lens support or mount. Optionally, the mount device 406 may comprise any variety of optical component mounts, supports, posts, rods, translation stages, stages, plates, and the like. In some embodiments, the optical component 400 is positioned within an optical component itself. For example, the optical component 400 may be positioned within a housing of a laser system thereby reducing or eliminating the effects of vibration therefrom. Further, the optical component 400 may be used to support any variety of vibration sensitive equipment in any variety of environments. For example, the optical component 400 may be secured or coupled to a support device used to support a spectral analyzer within the fuselage of an aircraft or a variety of other applications. In some embodiments, the body portion 402 of the optical component 400 may be made from materials such as aluminum, cast iron, carbon fiber, glass filled polymer or the like.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

What is claimed is:

1. An optical table with active vibration damping, comprising:
   a payload surface including at least one mounting feature; and
   an active vibration damper system including,
      a moveable active vibration damper assembly detachably coupled to the payload surface to allow an operator to detach and move the damper assembly to a different location of the payload surface to optimize the damping function of the assembly, the vibration damper assembly including a vibration sensor and an actuator, the actuator including an active element coupled to a mass and the mass being mechanically coupled by a flexure to the payload surface, and
      a controller which is in communication with the vibration sensor and actuator, and which is configured to generate a drive signal to the actuator that is configured to convert the drive signal into vibration motion applied to the payload surface to offset vibration in the payload surface as measured by the vibration sensor.

2. The optical table of claim 1 wherein the vibration sensor and actuator of the vibration damper assembly are coupled directly to the payload surface and are disposed within a single housing.

3. A moveable vibration damper assembly with active vibration damping, comprising:
   a housing,
   a base secured to the housing and configured to be detachably mounted onto a top surface of on a payload surface of an optical table by way of at least one mounting feature of the payload surface to allow an operator to detach and move the damper assembly to a different location of a payload surface to optimize the damping function of the assembly, and
   an actuator which is mechanically coupled to the housing, the actuator including an active element coupled to a mass and the mass being mechanically coupled by a flexure to the housing.

4. The assembly of claim 3 further comprising a vibration sensor mechanically coupled to the housing.

5. The assembly of claim 4 wherein the vibration sensor and actuator are disposed within a single housing.

6. The assembly of claim 4 further comprising a controller in communication with the actuator and the vibration sensor and configured to generate a drive signal to the actuator that converts the drive signal into vibration motion to offset vibration in the payload surface detachably mounted to the base as measured by the vibration sensor.

7. The assembly of claim 3 wherein the base comprises apertures configured to mate with threaded apertures of a mounting feature of a desired payload surface.

8. A moveable vibration damper assembly with active vibration damping, comprising:
   a housing,
   a base secured to the housing and configured to be detachably mounted onto a top surface of a payload surface of an optical table by way of at least one mounting feature of the payload surface to allow an operator to detach and move the damper assembly to a different location of a payload surface to optimize the damping function of the assembly, and
   an active vibration damper assembly coupled to the housing including a vibration sensor and an actuator, the actuator including an active element coupled to a mass, the mass being mechanically coupled by a flexure to the housing.

9. The assembly of claim 8 wherein the vibration sensor and actuator are disposed within a single housing.

10. The assembly of claim 9 further comprising a controller in communication with the active damper assembly and configured to generate a drive signal to the actuator that converts the drive signal into vibration motion to offset vibration in a payload surface detachably mounted to the base as measured by the vibration sensor.

* * * * *

UNITED STATES PATENT AND TRADEMARK OFFICE
CERTIFICATE OF CORRECTION

Page 1 of 1

PATENT NO.        : 8,231,098 B2
APPLICATION NO.   : 11/293439
DATED             : July 31, 2012
INVENTOR(S)       : Vyacheslav M. Ryaboy, Prakash S. Kasturi and Adrian S. Nastase It is certified that error appears in the above-identified patent and that said Letters Patent is hereby corrected as shown below:

In the Claims:

Column 20
 Claim 3, line 3 should read:
  "ably mounted onto a top surface of a payload surface"

Signed and Sealed this
Eighth Day of March, 2016

Michelle K. Lee
*Director of the United States Patent and Trademark Office*